(12) United States Patent
Taketomi et al.

(10) Patent No.: US 11,644,406 B2
(45) Date of Patent: May 9, 2023

(54) CALIBRATED FOCUS SENSING

(71) Applicant: Omniome, Inc., San Diego, CA (US)

(72) Inventors: Yoshinao Taketomi, San Diego, CA (US); Dale Buermann, San Diego, CA (US); Maxim Abashin, San Diego, CA (US); Donald V. Rosenberry, Oceanside, CA (US)

(73) Assignee: PACIFIC BIOSCIENCES OF CALIFORNIA, INC., Menlo Park, CA (US)

( * ) Notice: Subject to any disclaimer, the term of this patent is extended or adjusted under 35 U.S.C. 154(b) by 369 days.

(21) Appl. No.: 16/899,201

(22) Filed: Jun. 11, 2020

(65) Prior Publication Data
US 2020/0393353 A1  Dec. 17, 2020

Related U.S. Application Data

(60) Provisional application No. 62/859,886, filed on Jun. 11, 2019.

(51) Int. Cl.
 *G02B 21/24* (2006.01)
 *G02B 21/26* (2006.01)
 (Continued)

(52) U.S. Cl.
 CPC ....... *G01N 15/1434* (2013.01); *C12Q 1/6874* (2013.01); *G01M 11/0257* (2013.01);
 (Continued)

(58) Field of Classification Search
 CPC .......... G01N 15/1434; G01N 21/8806; C12Q 1/6874; G01M 11/0257; G02B 21/0016;
 (Continued)

(56) References Cited

U.S. PATENT DOCUMENTS

2008/0135724 A1* 6/2008 Hsu .................. G02B 21/247
                                                          250/201.3
2008/0247023 A1* 10/2008 Bloch ............... G02B 27/0905
                                                          359/223.1
(Continued)

FOREIGN PATENT DOCUMENTS

EP   2975444 A1   1/2016
EP   3158385 A1   4/2017

OTHER PUBLICATIONS

PCT/US2020/037268, "International Preliminary Report on Patentability", dated Dec. 23, 2021, 9 pages.
(Continued)

*Primary Examiner* — Mustak Choudhury
(74) *Attorney, Agent, or Firm* — Kilpatrick Townsend & Stockton LLP

(57) ABSTRACT

An apparatus for evaluating focus, including (a) a stage configured to hold a specimen; and (b) an optical train including a radiation source, calibration optic, objective and detector, the optical train forming a first path wherein radiation from the radiation source is directed to the calibration optic and then a first portion of the radiation is directed to the detector, thereby forming a first image on the detector, wherein a second portion of the radiation follows a second path from the calibration optic then through the objective to the specimen, wherein the optical train forms a third path wherein radiation reflected from the specimen is transmitted through the objective, then to the detector, thereby forming a second image on the detector, and wherein the radiation that forms the first image is astigmatic.

22 Claims, 16 Drawing Sheets

(51) Int. Cl.
*G01N 15/14* (2006.01)
*C12Q 1/6874* (2018.01)
*G01M 11/02* (2006.01)
*G02B 21/16* (2006.01)

(52) U.S. Cl.
CPC .......... *G02B 21/16* (2013.01); *G02B 21/244* (2013.01); *G02B 21/26* (2013.01)

(58) Field of Classification Search
CPC ........ G02B 21/02; G02B 21/06; G02B 21/16; G02B 21/24; G02B 21/26; G02B 21/244; G02B 21/245; G02B 21/247; G02B 21/361; G02B 21/365; G02B 7/09; G02B 7/32; G02B 7/38; G03B 13/36
See application file for complete search history.

(56) References Cited

U.S. PATENT DOCUMENTS

| | | | |
|---|---|---|---|
| 2008/0316898 A1* | 12/2008 | Itoh ..................... | G02B 21/006 |
| 2013/0329233 A1* | 12/2013 | Cohen ................ | G01M 11/0228 |
| | | | 356/624 |
| 2014/0152796 A1 | 6/2014 | Mitsuhiro et al. | |
| 2017/0199367 A1* | 7/2017 | Müller ................ | G02B 21/245 |
| 2017/0289412 A1* | 10/2017 | Staker .................. | G02B 21/16 |

OTHER PUBLICATIONS

Cohen et al., "Automatic Focus Control: The Astigmatic Lens Approach", Applied Optics, vol. 23, No. 4, Feb. 15, 1984, pp. 565-570.

PCT/US2020/037268, International Search Report and Written Opinion, dated Sep. 9, 2020, 13 pages.

* cited by examiner

CALIBRATED FOCUS SENSING

CROSS-REFERENCES TO RELATED APPLICATIONS

This application is based on, and claims the benefit of, U.S. Provisional Application No. 62/859,886, filed Jun. 11, 2019, and which is incorporated herein by reference.

BACKGROUND

The present disclosure relates generally to automatic focusing in optical detection systems and has specific applicability to automated microscopy systems such as those employed for detecting arrays of nucleic acids and other analytes.

Automated microscopy systems are generally equipped with one or more motor-actuated components and a programmable control mechanism that controls the functions of the system and operates one or more motor-actuators to set or modify operational conditions of the microscope. Exemplary operational conditions include, but are not limited to, focus, illumination intensity, exchange of optical filters, and specimen position. A control mechanism can function to automatically focus the microscope by generating control signals that cause relative movement between a stage (which positions a specimen that is under observation) and an objective (i.e. the optical component that is proximal to the specimen). Two common types of autofocus mechanisms are image-based autofocus and reflection-based autofocus.

Image-based autofocus uses a value obtained by transformation of an acquired image to indicate a degree of focus or sharpness. For example, a stage can be operated to place a specimen at a fixed xy location (i.e. fixed with respect to x and y coordinates in a Cartesian coordinate system) and the stage can be moved vertically through a succession of positions in the z dimension of the Cartesian coordinate system. At a first z position, an image is obtained from the specimen, and the image is transformed to obtain a first value from the image that is characteristic of the degree of focus. A second value is obtained by the same transformation of another image acquired at a second z position. More values are typically obtained at additional z positions. The values can then be compared, and an automated stage controller can be operated to move the stage to a vertical position where the values indicate the best degree of focus has been obtained.

Reflection-based autofocus uses a light signal that is generated by the optical system, projected through the objective toward the specimen, and reflected by a surface of the vessel that contains the specimen (or in some cases the light is reflected by the specimen itself), back through the objective. A desired focus location for the sample can be obtained by comparing a detected characteristic of the light signal with a predefined characteristic that is indicative of the degree of focus. For example, astigmatic focus exploits changes in the shape of the reflected image, and comparison of the shape to known correlations between shape and focus position, to determine when desired focus has been achieved.

Automated imaging with high resolution microscopic detection systems benefit from autofocus technologies that perform with submicron accuracy and precision. Both image-based autofocus and reflective positioning exhibit shortcomings that can compromise performance in particular applications. Image-based autofocus is generally accurate, but it is slow. Moreover, for specimens that are sensitive to light, for example, being prone to photodegradation or light-induced changes of state, image based autofocus can adversely impact the quality and veracity of subsequently acquired analytical images, independent of whether or not the analytical images are well focused. Because image-based autofocus utilizes the sample itself, samples that are highly variable in morphology, for example, including voids that appear as empty fields of view, can be troublesome to focus. Reflective positioning can be sensitive to the calibration of the optical system in use. For example, even small changes in temperature, or relatively minor physical disturbances to a microscope (e.g. bumping, vibrations etc.) can cause components of an autofocus system to change position. These changes, if not accounted for, can result in a misdiagnosis of focus and inability of a system to find focus.

Thus, there exists a need for robust and accurate autofocus technologies that overcome weaknesses of existing technologies. Certain embodiments described satisfy this need and/or provide related advantages.

BRIEF SUMMARY

The present disclosure provides an apparatus for evaluating focus. The apparatus can include (a) a stage configured to hold a specimen; and (b) an optical train including a radiation source, calibration optic, objective and detector, the optical train forming a first path wherein radiation from the radiation source is directed to the calibration optic and then a first portion of the radiation is directed to the detector, thereby forming a first image on the detector, wherein a second portion of the radiation follows a second path from the calibration optic then through the objective to the specimen, wherein the optical train forms a third path wherein radiation reflected from the specimen is transmitted through the objective, then to the detector, thereby forming a second image on the detector, and wherein the radiation that forms the first image is astigmatic.

The present disclosure also provides an apparatus for evaluating focus that includes (a) a stage configured to hold a specimen; and (b) an optical train comprising a radiation source, collimator, primary beam splitter, calibration beam splitter, objective and detector, the optical train forming a first path wherein radiation from the radiation source is collimated by the collimator, then transmitted to the primary beam splitter, then to the calibration beam splitter, then a first portion of the radiation continues on the first path from the calibration beam splitter to the primary beam splitter, then to the detector, thereby forming a first image on the detector, wherein a second portion of the radiation follows a second path from the calibration beam splitter then through the objective to the specimen, wherein the optical train forms a third path wherein radiation from the specimen is transmitted through the objective, then through the calibration beam splitter, then through the primary beam splitter, then to the detector, thereby forming a second image on the detector, and wherein the optical train comprises an astigmatism generator between the radiation source and the calibration beam splitter. Optionally, the astigmatism generator is a toric surface of the primary beam splitter, the toric surface configured for transmitting radiation from the collimator to the calibration beam splitter. In another option, the astigmatism generator is an astigmatic lens, such as a cylindrical lens or a crossed cylindrical lens pair, positioned between the radiation source and the calibration beam splitter in the optical train.

The present disclosure also provides an apparatus for evaluating focus that includes (a) a stage configured to hold a specimen; and (b) an optical train comprising a radiation source, collimator, primary beam splitter, calibration beam splitter, objective and detector, the optical train forming a first path wherein radiation from the radiation source is collimated by the collimator, then transmitted to the primary beam splitter, then to the calibration beam splitter, then a first portion of the radiation continues on the first path from the calibration beam splitter to the primary beam splitter, then to the detector, thereby forming a first image on the detector, wherein a second portion of the radiation follows a second path from the calibration beam splitter then through the objective to the specimen, wherein the optical train forms a third path wherein radiation from the specimen is transmitted through the objective, then through the calibration beam splitter, then through the primary beam splitter, then to the detector, thereby forming a second image on the detector, and wherein the primary beam splitter has a toric surface for transmitting radiation from the collimator to the calibration beam splitter, or the optical train includes an astigmatic lens between the radiation source and the calibration beam splitter.

The present disclosure also provides a focusing method. The method can include steps of (a) transmitting radiation through a focusing apparatus to a calibration optic that directs a first portion of the radiation to a detector, thereby forming a first image on the detector, wherein the radiation that forms the first image is astigmatic; (b) transmitting a second portion of the radiation from the calibration optic through an objective to a vessel, wherein radiation is reflected from the vessel; (c) transmitting the reflected radiation through the objective, then to the detector, thereby forming a second image on the detector; (d) determining a calibration state for the focusing apparatus from the first image; (e) determining a focus correction from the second image and from the calibration state; and (f) adjusting the relative position of the objective and the vessel according to the focus correction.

The present disclosure also provides a focusing method that includes steps of (a) transmitting collimated radiation through a focusing apparatus to a primary beam splitter, then to a calibration beam splitter, wherein a first portion of the radiation from the calibration beam splitter is transmitted by the primary beam splitter, to form a first image on a detector, wherein an astigmatism is generated in the collimated radiation prior to being transmitted to the calibration beam splitter; (b) transmitting a second portion of the radiation from the calibration beam splitter through an objective to a vessel, wherein radiation is reflected from the vessel; (c) transmitting the reflected radiation through the objective, then through the calibration beam splitter, then through the primary beam splitter to form a second image on a detector; (d) determining a calibration state for the focusing apparatus from the first image; (e) determining a focus correction from the second image and from the calibration state; and (f) adjusting the relative position of the objective and the vessel according to the focus correction.

The present disclosure also provides a focusing method that includes steps of (a) transmitting collimated radiation through a focusing apparatus to a primary beam splitter, then to a calibration beam splitter, wherein a first portion of the radiation from the calibration beam splitter is transmitted to the primary beam splitter, then to a detector, thereby forming a first image on the detector, wherein the primary beam splitter has a toric surface for transmitting radiation from the collimator to the calibration beam splitter, or the optical train includes an astigmatic lens between the radiation source and the calibration beam splitter; (b) transmitting a second portion of the radiation from the calibration beam splitter through an objective to a vessel, wherein radiation is reflected from the vessel; (c) transmitting the reflected radiation through the objective, then through the calibration beam splitter, then through the primary beam splitter, then to the detector, thereby forming a second image on the detector; (d) determining a calibration state for the focusing apparatus from the first image; (e) determining a focus correction from the second image and from the calibration state; and (f) adjusting the relative position of the objective and the vessel according to the focus correction.

DETAILED DESCRIPTION

Figure 1A:
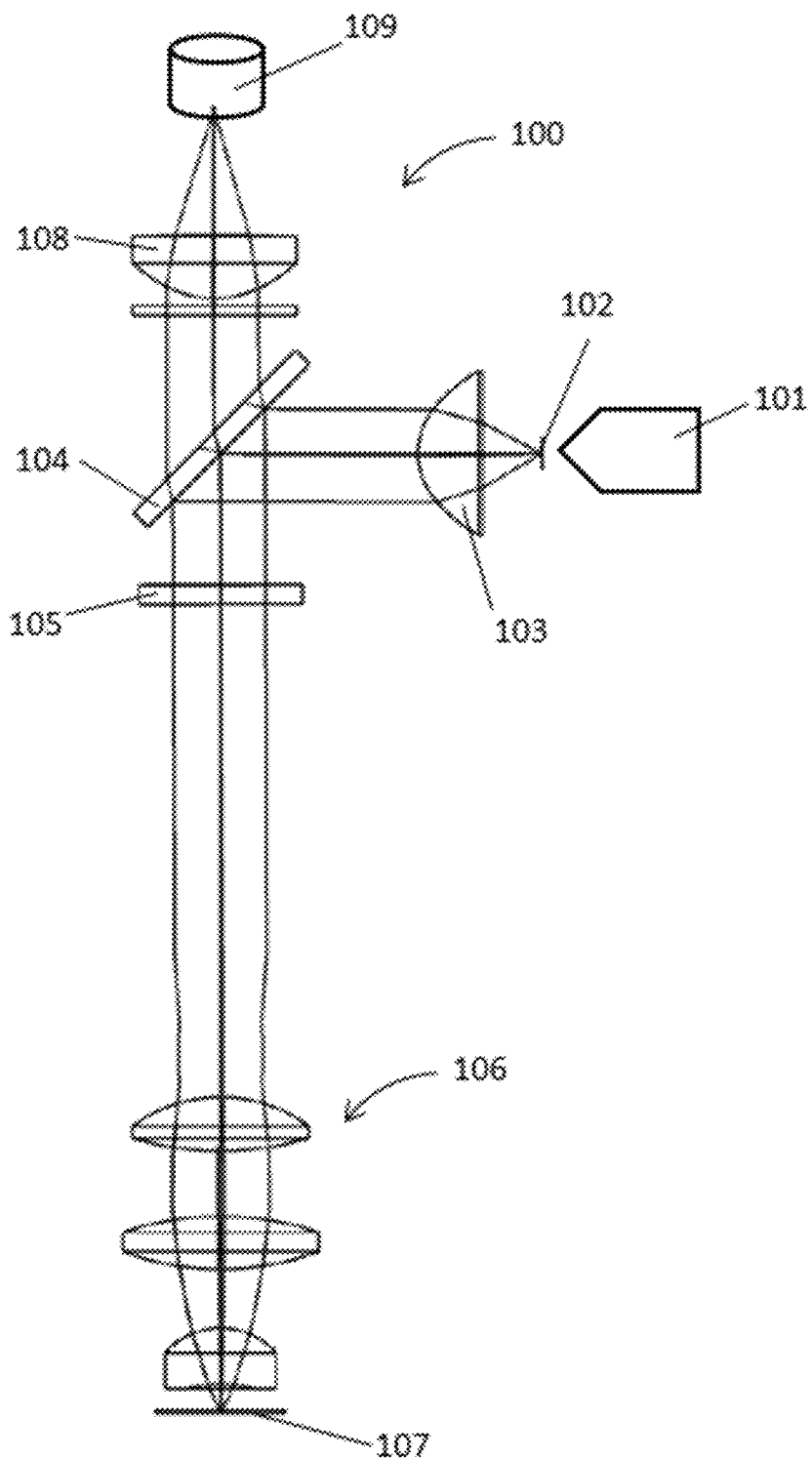
FIG. 1A shows a diagrammatic representation of a focus sensing optical train having a toric beam splitter as an astigmatic element.

The present disclosure provides a focus sensing apparatus and method that can be used to evaluate degree of focus for an optical detection system or method. The focus sensing apparatus or method can optionally participate in an autofocus apparatus or method by informing an error detection circuit that instructs an actuator circuit to adjust the system to change the distance between a specimen and the optical system that observes the specimen.

Particular configurations of the focus sensing apparatus and methods utilize reflection-based focus sensing. This configuration is particularly beneficial when applied to detection of luminescently labeled biological components since such components are often sensitive to the radiation that is used to excite the luminescent labels. For example, luminescent labels are prone to produce highly reactive radical species (e.g. singlet oxygen) that degrade nucleic acids, proteins, and other analytes of interest. Reducing exposure to radiation can be especially beneficial for cyclical, luminescence-based nucleic acid sequencing methods because the nucleic acids are exposed to radiation during each detection cycle. Typically, each nucleotide in the sequence is detected in a cycle. Accumulated damage to the nucleic acids over the cycles will adversely impact read length and accuracy for sequencing. Other analytical processes that utilize repeated exposure of analytes to radiation can be adversely impacted in similar ways. The use of reflection-based focus sensing is beneficial for avoiding photodamage since the nucleic acids or other analytes of interest need not be exposed to the radiation that is used to focus the vessel within which they are contained. A reflection-based focusing system can also provide faster analytical detection since autofocus can be carried out in parallel with analytical detection rather than needing to perform autofocus in a separate protocol that would have been carried out prior to analytical detection.

Particular configurations of the focus sensing apparatus and methods include automatic calibration of the focusing sensing apparatus in use. The automatic calibration capability set forth herein provides diagnostic information regarding any variance in the focus sensing apparatus itself that impacts the accuracy of the autofocus determination. Variance can occur due to a variety of conditions that are not atypical for an analytical detection system to encounter including, for example, temperature or humidity changes that result in expansion or contraction of optical elements, vibrations or physical impacts that alter position of optical elements, or the like. Such changes in position may occur due to changes in the optical components themselves or due to changes in the mounts that orient the optical components with respect to each other. Typical focus systems can be calibrated to adjust for variance in the focus sensing system itself, for example, by performing a focus calibration protocol whereby the distance between the stage and objective is systematically stepped through several levels within a range while measuring focus. The z position that is found to provide best focus position in this empirical process is then set by the system as the focus position. Although use of this type of empirical focus calibration method can be quite accurate, it is time consuming and comes with increased risk of exposing the specimen to unwanted radiation from the focus sensing system. In contrast, the automatic calibration apparatus and methods set forth in the present disclosure allow calibration state to be sensed and adjusted while focus sensing is performed and without necessarily performing a calibration protocol that interrupts analytical detection that is the primary function of the instrument.

The present disclosure provides an apparatus for evaluating focus. The apparatus can include (a) a stage configured to hold a specimen; and (b) an optical train comprising a radiation source, collimator, primary beam splitter, calibration beam splitter, objective and detector, the optical train forming a first path wherein radiation from the radiation source is collimated by the collimator, then transmitted to the primary beam splitter, then to the calibration beam splitter, then a first portion of the radiation continues on the first path from the calibration beam splitter to the primary beam splitter, then to the detector, thereby forming a first image on the detector, wherein a second portion of the radiation follows a second path from the calibration beam splitter then through the objective to the specimen, wherein the optical train forms a third path wherein radiation from the specimen is transmitted through the objective, then through the calibration beam splitter, then through the primary beam splitter, then to the detector, thereby forming a second image on the detector, and wherein the optical train comprises an astigmatism generator between the radiation source and the calibration beam splitter. Optionally, the astigmatism generator is a toric surface of the primary beam splitter, the toric surface configured for transmitting radiation from the collimator to the calibration beam splitter. In another option, the astigmatism generator is an astigmatic lens, such as a cylindrical lens or a crossed cylindrical lens pair, positioned between the radiation source and the calibration beam splitter in the optical train.

The present disclosure also provides a focusing method. The method can include steps of (a) transmitting collimated radiation through a focusing apparatus to a primary beam splitter, then to a calibration beam splitter, wherein a first portion of the radiation from the calibration beam splitter is transmitted by the primary beam splitter to form a first image on the detector, wherein an astigmatism is generated in the collimated radiation prior to being transmitted to the calibration beam splitter; (b) transmitting a second portion of the radiation from the calibration beam splitter through an objective to a vessel, wherein radiation is reflected from the vessel; (c) transmitting the reflected radiation through the objective, then through the calibration beam splitter, then through the primary beam splitter to form a second image on a detector; (d) determining a calibration state for the focusing apparatus from the first image; (e) determining a focus correction from the second image and from the calibration state; and (f) adjusting the relative position of the objective and the vessel according to the focus correction.

An exemplary optical train 100 for evaluating autofocus and calibration of the optical train is shown in FIG. 1A. Calibration can be determined from an image produced by a first path through the optical train 100. More specifically, radiation is produced by a radiation source 101 (e.g., a light emitting diode (LED)) and passes through pinhole 102 to create a point source for radiation entering the rest of the optical train 100. The radiation is then collimated by collimator 103 and transmitted to toric beam splitter 104 where at least a portion of the radiation is reflected to calibration beam splitter 105. A portion of the radiation is reflected by the calibration beam splitter 105 such that it passes through toric beam splitter 104, then through an imaging lens 108 to detector 109. The product of this first path is an image on the detector that is indicative of the calibration state of the optical train. The first path is an example of a calibration sensing path.

As set forth above, a portion of the radiation that was reflected to the calibration beam splitter 105 by the toric beam splitter 104 will be reflected back to the toric beam splitter 104. Another portion of the radiation that was reflected by the toric beam splitter 104 will follow a second path, whereby the radiation passes through the calibration beam splitter 105 to the objective 106 and then to a specimen that is positioned on the stage 107. As such, the second path can be considered to include the path from radiation source 101, through pinhole 102, through collimator 103, reflected by toric beam splitter 104, through calibration beam splitter 105, through objective 106 and to the specimen on stage 107. Radiation from the second path can be reflected by the specimen and the reflected radiation can be transmitted along a third path through the objective 106, through calibration beam splitter 105, through toric beam splitter 104, through imaging lens 108 to detector 109. The product of this third path is an image on the detector that is indicative of the focus state of the optical train 100. The combined second and third paths function as a focus sensing path.

The optical train 100 shown in FIG. 1A is an exemplary configuration for achieving the functions set forth herein. It will be understood that other configurations can be used. For example, optical components having similar properties can be swapped out. Similarly, the configuration of the exemplified optical components (or functionally equivalent components) can be modified to produce images that are indicative of calibration state and focus state. Looking to the optical train 100 of FIG. 1A, collimator 103 can be omitted if the toric beam splitter 104 is replaced with a dual axis reflector such as an optical component having an off-axis parabola or dual axis aspheric surface. Moreover, pinhole 102 can be omitted by using a highly collimated laser as a radiation source and collimator 103 can function as a beam expander to expand the laser beam, but need not function as a collimator. Similar modifications can be made with regard to collimators, pinholes and radiation sources exemplified in other optical trains set forth herein.

Figure 2A:
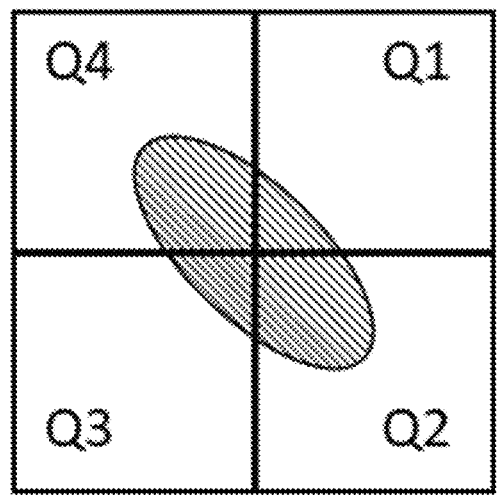
FIG. 2 shows representations of astigmatic images captured on a four quadrant detector when an optical system is in focus (FIG. 2B) or out of focus in opposite directions (FIG. 2A and FIG. 2C).
Figure 2B:
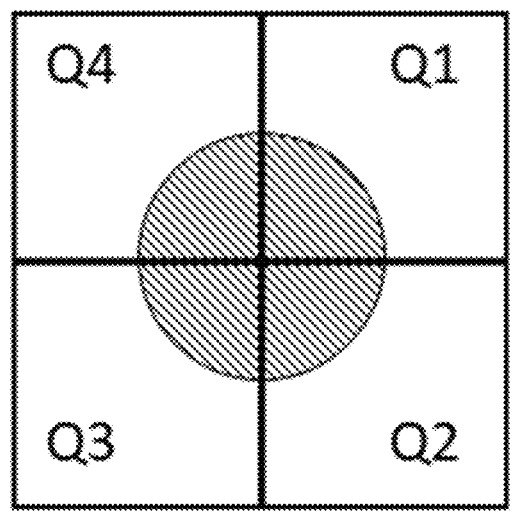
Figure 2C:
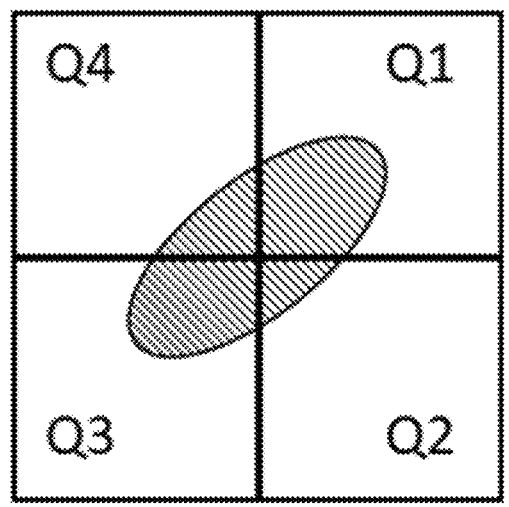

An apparatus or method of the present disclosure can be configured for astigmatic focus sensing. Astigmatic focus sensing employs an optical system having a known astigmatism that is sensitive to the focal distance between the optics and the specimen being viewed by the optical system. For example, light can be directed through an astigmatic optical train to the surface of a vessel, such as a slide or flow cell, and an image of the light that is reflected by the vessel can be detected. The astigmatism can be introduced at any of a variety of positions in the optical train as set forth in further detail below. Particular characteristics of the image, such as shape or intensity, can be correlated with the focal distance due to the nature of the astigmatism. In the example shown in FIG. 2, an optical system that is in focus will create a circular light spot on a camera (see FIG. 2B), whereas deviations from focus will create a light spot that is elliptical on the camera. In this example, the camera has four quadrants (Q1 through Q4) and the image is centered at the intersection of the four quadrants such that the circular image results in detection of roughly equivalent intensity from each quadrant. The direction that the image is elliptically elongated, indicates the direction for the deviation from focus. FIG. 2A shows an image that is elongated such that the intensity detected in Q2 and Q4 is higher than the intensity detected in Q1 and Q3, indicating, for example, that the vessel is too far from the objective to be in focus (i.e. moving the objective and vessel closer together will improve focus). In this example, an image that is elongated such that the intensity detected in Q1 and Q3 is higher than the intensity detected in Q2 and Q4 See FIG. 2C) indicates that the vessel is too close to the objective to be in focus (i.e. moving the objective and vessel further apart will improve focus). The degree to which the image is elongated will be indicative of the distance for the deviation from focus (i.e. the distance along the z dimension of a Cartesian coordinate system) and can be determined according to the magnitude of the intensity difference detected in each pair of quadrants in the detector. The deviation from focus can be quantitated according to Formula I:

$$F_D = (Q1_i + Q3_i) - (Q2_i + Q4_i), \quad \text{(Formula I)}$$

wherein $F_D$ is deviation from focus, $Q1_i$ is the intensity of radiation from the focus sensing optical path that is detected at quadrant 1, $Q2_i$ is the intensity of radiation from the focus sensing optical path that is detected at quadrant 2 etc. A z focus value (ZFV) can be calculated according to Formula II:

$$ZFV = F_D / (Q1_i + Q2_i + Q3_i + Q4_i), \quad \text{(Formula II)}$$

wherein $F_D$ is deviation from focus, $Q1_i$ is the intensity of radiation from the focus sensing optical path that is detected at quadrant 1, $Q2_i$ is the intensity of radiation from the focus sensing optical path that is detected at quadrant 2 etc.

The use of images that form circular/elliptical shapes on a quadrant detector is exemplary of principles that can be used when determining focus using astigmatic optics. Other detectors and other characteristics of astigmatic light that are indicative of focus can be used as well.

An apparatus or method of the present disclosure can be configured for astigmatic calibration sensing. As set forth in the figures and teachings of the present disclosure, a focus sensing apparatus can be configured with optical components that create a focus sensing path for astigmatic radiation, wherein an astigmatic image produced from the focus sensing path is indicative of the distance between the objective and specimen. A subset of the optical components can also create a calibration sensing path for the astigmatic radiation. An astigmatic image produced from the calibration sensing path will be indicative of the calibration state for those optical components that constitute the calibration sensing path. The astigmatic image (or other characteristic determined from the calibration sensing path) can be evaluated as exemplified herein for evaluating an image or other characteristic obtained from a focus sensing path. Accordingly, the deviation in calibration can be determined from Formula III:

$$C_D = (Q1_i + Q3_i) - (Q2_i + Q4_i), \quad \text{(Formula III)}$$

wherein $C_D$ is deviation in calibration, $Q1_i$ is the intensity of radiation from the calibration optical path that is detected at quadrant 1, $Q2_i$ is the intensity of radiation from the calibration optical path that is detected at quadrant 2 etc. A z calibration value (ZCV) can be calculated according to Formula IV:

$$ZCV = C_D / (Q1_i + Q2_i + Q3_i + Q4_i), \quad \text{(Formula IV)}$$

wherein $C_D$ is deviation in calibration, $Q1_i$ is the intensity of radiation from the calibration optical path that is detected at quadrant 1, $Q2_i$ is the intensity of radiation from the calibration optical path that is detected at quadrant 2 etc. A calibrated focus value can be detected by subtracting CD from FD. Alternatively, a calibrated focus value can be detected by subtracting ZCV from ZFV.

Astigmatic focus sensing can optionally participate in an automated feedback loop, whereby an error detection circuit evaluates the image produced by an astigmatic focus sensing path to determine the distance and direction of any deviation from focus, and instructions from the error detection circuit are sent to an actuator that adjusts the relative position of the specimen and the optical system in order to improve focus. Block diagrams of exemplary detection circuits for astigmatic focusing systems are shown in FIGS. 1B, 3B, 4B and 6B. In a further option, astigmatic focus sensing can participate in an automated feedback loop, whereby an error detection circuit evaluates the images produced by an astigmatic focus sensing path and the same or different error detection circuit evaluates the images produced by an astigmatic calibration sensing path. The combined information from the two images can be compared to determine the distance and direction of any deviation from focus, and instructions from the error detection circuit(s) are sent to an actuator that adjusts the relative position of the specimen and the optical system in order to improve focus.

The feedback loop can go through several iterations of image detection, evaluation of image characteristics and actuated movement to achieve focus for any given area that is to be imaged in a specimen (different areas that will be detected in a vessel or other specimen can be referred to as 'tiles'). The autofocus loop can be repeated for other tiles, for example, when a vessel or specimen is translated (i.e. along the x or y dimensions of a Cartesian coordinate system where focus occurs along the z dimension).

An astigmatism can be introduced into an optical system using any of a variety of optical components or methods. An optical system with astigmatism is one where rays that propagate in two perpendicular planes have different foci. In some configurations, the astigmatism can be introduced via use of an astigmatic radiation source upstream of a focus sensing system. Some configurations can utilize an astigmatic optical component at a position in a focus sensing optical path that is downstream of a radiation source and upstream of a detector used to detect the astigmatism. Astigmatism can be introduced by an optical component such as a cylindrical lens, optical component having surface shapes that introduce an astigmatism (e.g. a toric surface on a beam splitter), optical components having free form surfaces that introduce astigmatism, or "mis"-alignment of optical components that results in astigmatism (e.g. a crossed cylindrical lens pair). A particularly useful astigmatic optical component is an astigmatic lens having a bi-conic surface, which is a non-rotational symmetric surface, an example of which is set forth in Hsu et al., *Meas. Sci. Technol.* 20: 045902 (2009) (doi:10.1088/0957-0233/20/4/045902), which is incorporated herein by reference.

Another exemplary optical train for evaluating autofocus and calibration of the optical train is shown in FIG. 3. Calibration can be determined from an image produced by a first path through the optical train 300. More specifically, radiation is produced by radiation source 301 (e.g., an LED) and passes through collimator 303 to toric beam splitter 304 where at least a portion of the radiation is reflected to calibrator 305. A portion of the radiation is reflected by the calibrator 305 such that it passes through toric beam splitter 304, then through bandpass filter 311 and on to imaging lens 308 then detector 309. The product of this first path is an image on detector 309 that is indicative of the calibration state of the optical train. The first path is an example of a calibration sensing path. The calibration sensing path and the elements involved in the path are indicated by the dotted line arrow in FIG. 3C.

As set forth above, a portion of the radiation that was reflected to the calibrator 305 by the toric beam splitter 304 will be reflected back to the toric beam splitter 304. Another portion of the radiation that was reflected by the toric beam splitter 304 will follow a second path, whereby the radiation passes through the calibrator 305 then through compensator 312 to the objective 306, and then to a specimen that is positioned on the stage 307. As such, the second path can be considered to include the path from radiation source 301, through collimator 303, reflected by toric beam splitter 304, through calibrator 305, through objective 306 and to the specimen on stage 307. Radiation from the second path can be reflected by the specimen and the reflected radiation can be transmitted along a third path through the objective 306, through compensator 312, through calibrator 305, through toric beam splitter 304, through imaging lens 308 to detector 309. The product of this third path is an image on detector 309 that is indicative of the focus state of the optical train. The combined second and third paths function as a focus sensing path. The focus sensing path and the elements involved in the path are indicated by the dotted line arrow in FIG. 3D.

The calibration sensing path and the focus sensing path can be configured to produce separate images that can be individually evaluated. The images can be compared to calibrate the autofocus measurement for any of a variety of influences. For example, temperature sensitivities of the autofocus sensing path and the calibration sensing path can differ from each other in a known way. FIG. 3E shows exemplary images expected for the calibration sensing path at two temperatures indicated at T0 and T1. At T0 the image for the calibration sensing path is indicated as a grey circle and at T1 the image for the calibration sensing path is indicated as a grey oval. FIG. 3E also shows exemplary images expected for the focus sensing path at T0 and T1. At T0 the image for the focus sensing path is indicated as a black circle and at T1 the image for the calibration sensing path is indicated as a black oval. The shapes of the images for the calibration sensing path and focus sensing path can be related to each other according to the plot and formula shown in FIG. 3F. The black line plots metric for the focus sensing path (MF) vs. temperature and the grey line plots the metric for the calibration sensing path vs. temperature. Exemplary metrics include those set forth herein in the context of FIG. 2 or otherwise known in the art pertaining to autofocus algorithms. The relationship between the two lines can be used to calibrate and correct focus for aberrations caused by temperature changes in the optical system. In this example, the best focus is achieved when the function f=0.

Objective 306 and related optical components that can be used in an apparatus or method set forth herein are set forth in U.S. Pat. No. 10,656,368, which is incorporated herein by reference. In an exemplary configuration, an objective lens can have a depth of field equal to or less than 1.5 microns. The objective lens can include: a first doublet lens having a first lens and a second lens, wherein: the first lens of the first doublet lens has a concave and a convex surface, and the second lens of the first doublet lens has a concave and a convex surface; a second doublet lens having a first lens and a second lens, wherein: the first lens of the second doublet lens has a concave and a convex surface, and the second lens of the second doublet lens has a concave and a convex surface; a third doublet lens having a first lens and a second lens, wherein: the first lens of the third doublet lens has two convex surfaces, the second lens of the third doublet lens has two concave surfaces, and the second doublet lens is between the first doublet lens and the third doublet lens; a fourth doublet lens having a first lens and a second lens, wherein: the first lens of the fourth doublet lens has two concave surfaces, the second lens of the fourth doublet lens has two convex surfaces, the third doublet lens is between the second doublet lens and the fourth doublet lens, the first doublet lens is a first lens of an optical train of the objective lens and the fourth doublet lens is a last lens of the optical train of the objective lens, the first doublet lens is configured to be closer to the solid support than the fourth doublet lens, and/or optical rays are not infinity corrected after passing from the first doublet lens through the fourth doublet lens; a first singlet lens between the second doublet lens and the third doublet lens, the first singlet lens having two convex surfaces; a second singlet lens between the second doublet lens and the third doublet lens, the second singlet lens having two convex surfaces; an aspheric lens between the third doublet lens and the fourth doublet lens, wherein the aspheric lens has a diameter equal to or greater than 40 millimeters and equal to or less than 60 millimeters; and/or an aperture stop between the third doublet lens and the fourth doublet lens, wherein: the aperture stop is a physical aperture stop having one or more walls forming an opening, the aperture stop is within 25 millimeters of the aspheric lens, and/or the aperture stop is located at a distance between 70% and 90% in the optical train measured from the first doublet lens. In some embodiments, the objective lens has no more than 22 surfaces of lenses that affect optical power of the objective lens, 16 surfaces from four doublet lenses, four surfaces from two singlet lenses, and two surfaces from the aspheric lens; optical elements of the objective lens consist of four doublet lenses, two singlet lenses, the aspheric lens, and the aperture stop; and/or the solid support is part of a flow cell, the flow cell comprises a cover slip, and the cover slip is 1 millimeter thick.

In some configurations, an objective lens includes a plurality of lenses having simple surfaces, wherein: the plurality of lenses form an optical train, the optical train extending from a first lens to a last lens, and the plurality of lenses include four doublet lenses and no triplet lenses; an aperture stop, wherein: the aperture stop is a physical aperture stop, and the aperture stop is located between the first lens and the last lens; and/or an aspheric lens between the first lens and the last lens, the aspheric lens positioned within 25 millimeters of the aperture stop. In some configurations, the first lens is configured to be closer to a specimen than the last lens; the aperture stop is located at a distance between 70% and 90% in the optical train as measured from the first lens; optical rays are not infinity corrected after passing through the last lens of the optical train; the aspheric lens has a diameter equal to or greater than 40 millimeters and equal to or less than 60 millimeters; the apparatus has a depth of field equal to or less than 1.5 microns; the apparatus has a numerical aperture between 0.6 and 0.8; and/or the apparatus has a field of view that is at least 1 mm².

Figure 3A:
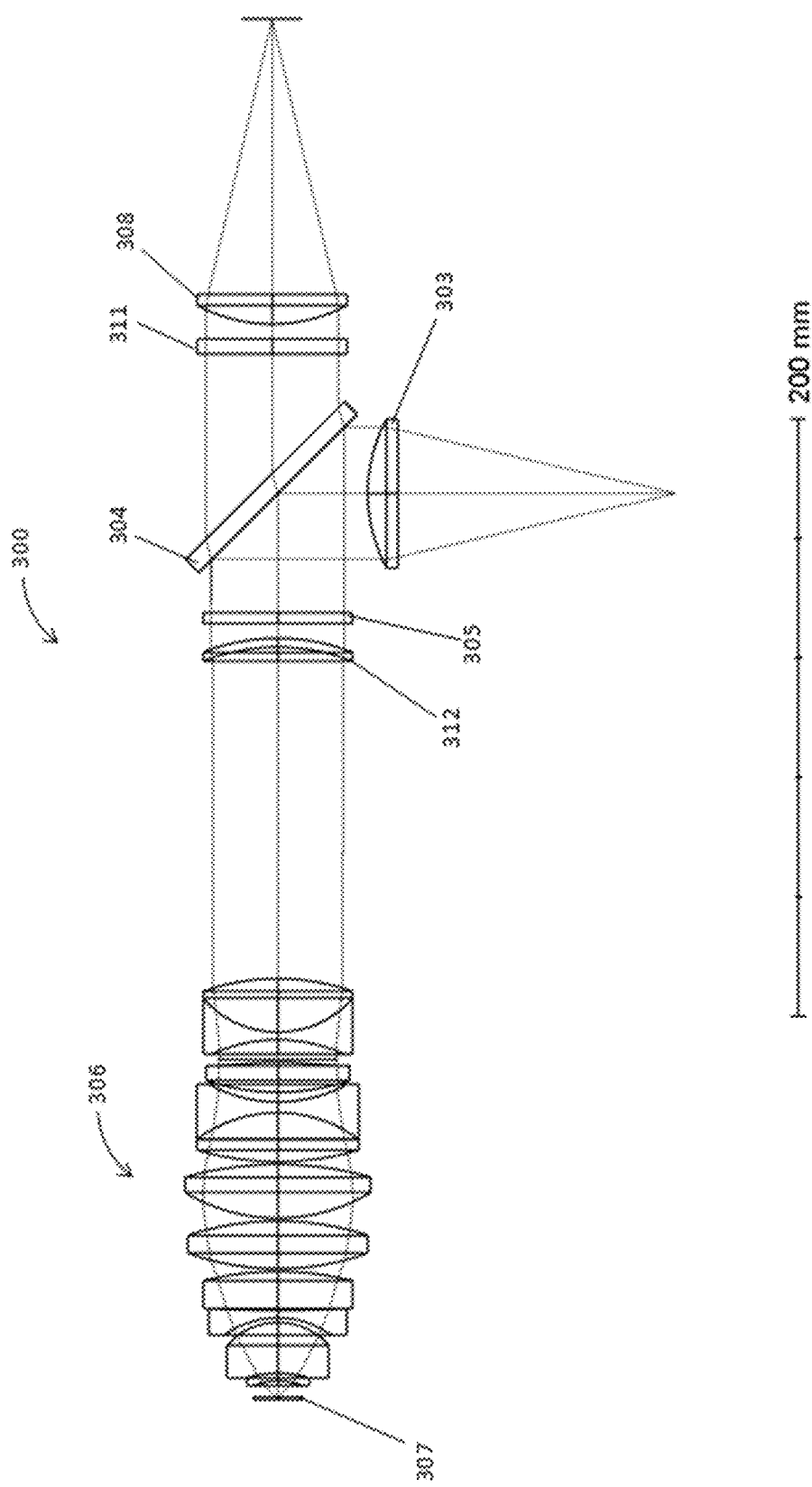
FIG. 3A shows a diagrammatic representation of a focus sensing optical train having a toric beam splitter as an astigmatic element.

The configurations shown in FIG. 1A and FIG. 3A provide examples of introducing an astigmatism via an optical component having a toric surface. In these examples, the toric surface is on the primary beam splitter such that light that is reflected by the surface will have an astigmatism that is responsive to movements in other optical components downstream and upstream of the toric surface. In the configurations of FIG. 1A and FIG. 3A, the toroidal radius of the toric surface can optionally be between 2000 mm and 5000 mm. A toric beam splitter can provide advantages as a generator of astigmatism in a focus sensing apparatus since it has different influence on radiation that reflects from its toric surface compared to its influence on radiation that transmits through the toric surface. The toric surface of toric beam splitter 104 introduces astigmatism into the radiation that is reflected to calibration beam splitter 105. Similarly, the toric surface of toric beam splitter 304 introduces astigmatism into the radiation that is reflected to calibrator 305. However, the toric surface can be configured and positioned such that it does not introduce astigmatism to radiation that is transmitted through it for one or both of the exemplified optical trains.

As an alternative to using a toric beam splitter to introduce astigmatism into a focus sensing optical train, the optical train of a focus sensing apparatus can include an astigmatic lens placed between the radiation source and the stage. Taking the exemplary configuration of FIG. 1A, the toric beam splitter can be replaced with a non-toric beam splitter and an astigmatic lens (e.g. a cylindrical lens) can be placed between the radiation source and the collimator, or between the collimator and the non-toric beam splitter, or between the non-toric beam splitter and the calibration beam splitter, or between the calibration beam splitter and the objective.

Figure 4A:
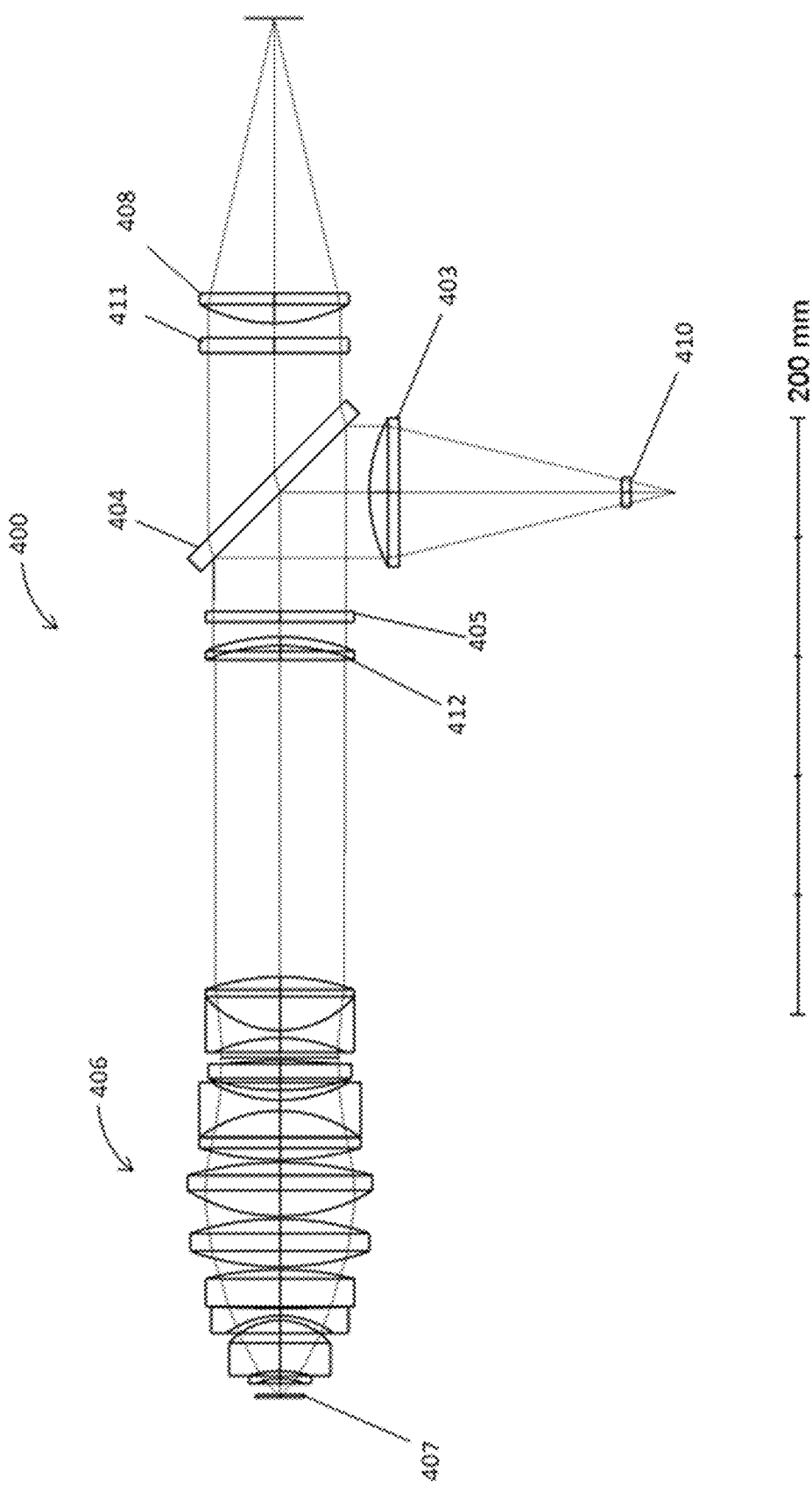
FIG. 4A shows a diagrammatic representation of a focus sensing optical train having a cylindrical lens as an astigmatic element.
Figure 4B:
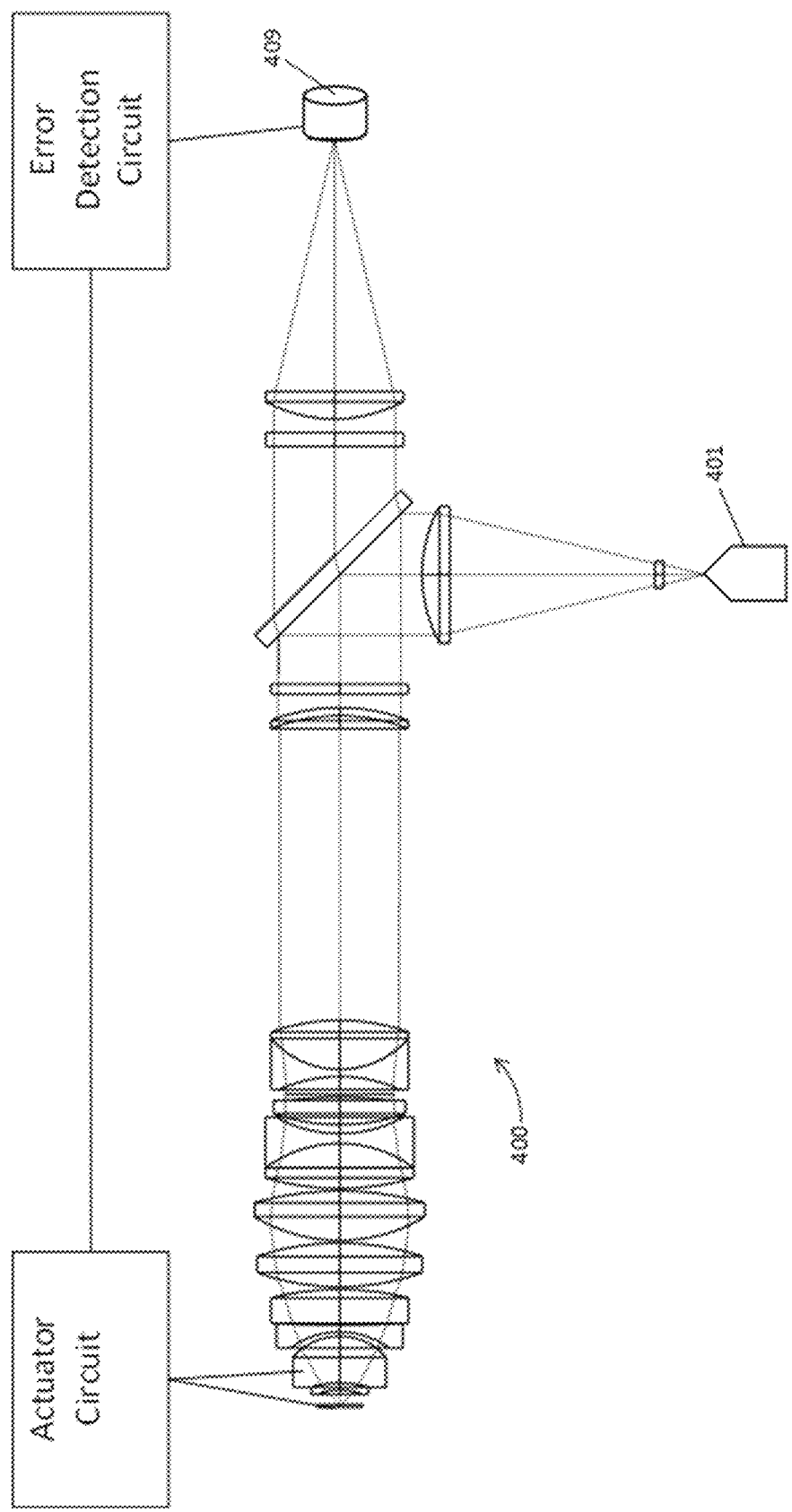
FIG. 4B shows a diagrammatic representation of an autofocus system that includes a focus sensing optical train having a cylindrical lens as an astigmatic element.

FIGS. 4A and 4B show an optical train that uses a cylindrical lens to introduce an astigmatism for evaluating autofocus and calibration of the optical train. Calibration can be determined from an image produced by a first path through the optical train 400. More specifically, radiation is produced by radiation source 401 (e.g., an LED) and passes through cylindrical lens 410, to collimator 403 and then to beam splitter 404 where at least a portion of the radiation is reflected to calibrator 405. Beam splitter 404 does not have a toric surface in this example. A portion of the radiation is reflected by the calibrator 405 such that it passes through beam splitter 404, then through bandpass filter 411 and on to imaging lens 408 then detector 409. The product of this first path is an image on detector 409 that is indicative of the calibration state of the optical train. The first path is an example of a calibration sensing path.

As set forth above, a portion of the radiation that was reflected to the calibrator 405 by the beam splitter 404 will be reflected back to the beam splitter 404. Another portion of the radiation that was reflected by the beam splitter 404 will follow a second path, whereby the radiation passes through the calibrator 405 then through compensator 412 to the objective 406, and then to a specimen that is positioned on the stage 407. As such, the second path can be considered to include the path from radiation source 401, through cylindrical lens 410, through collimator 403, reflected by beam splitter 404, through calibrator 405, through objective 406 and to the specimen on stage 407. Radiation from the second path can be reflected by the specimen and the reflected radiation can be transmitted along a third path through the objective 406, through compensator 412, through calibrator 405, through beam splitter 404, through imaging lens 408 to detector 409. The product of this third path is an image on detector 409 that is indicative of the focus state of the optical train. The combined second and third paths function as a focus sensing path.

Figure 5:
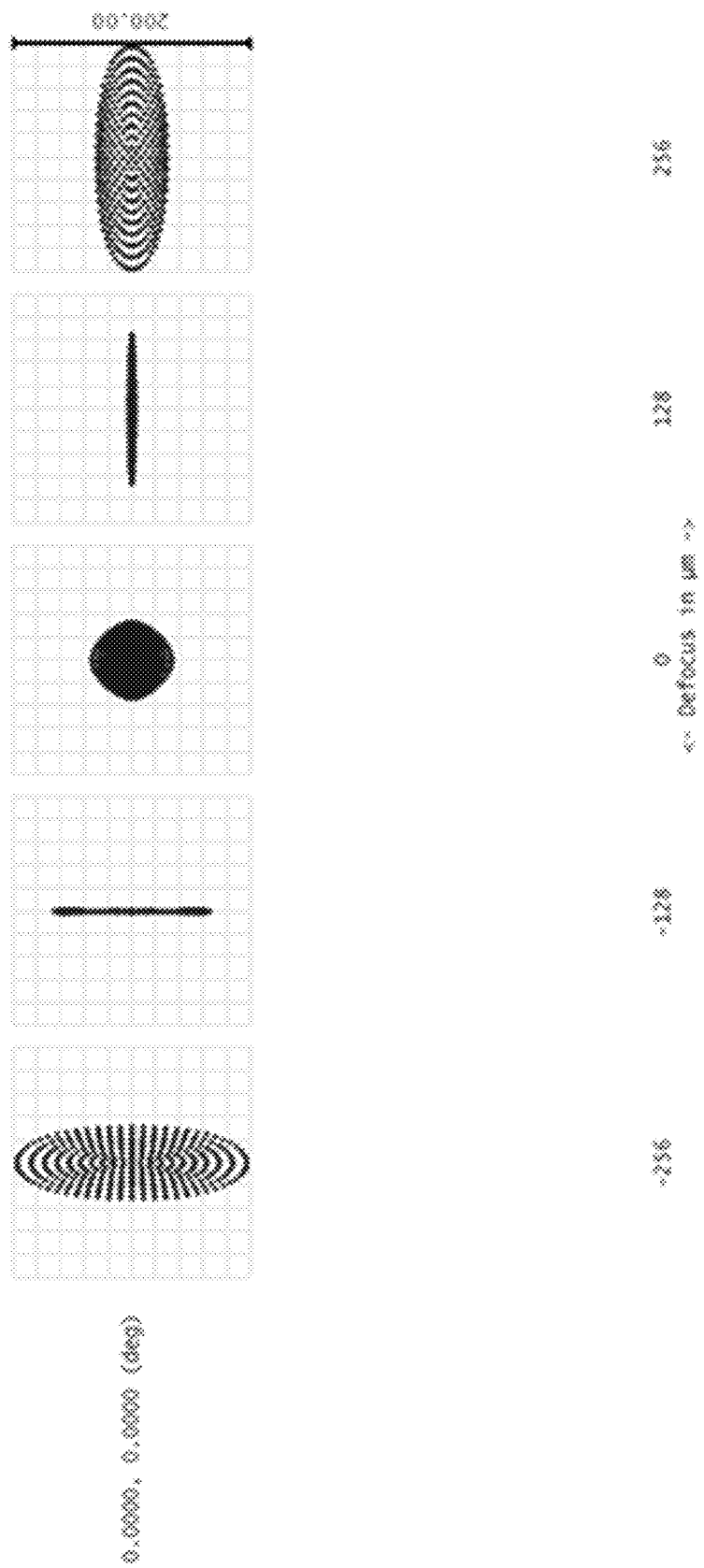
FIG. 5 shows images expected for various focus deviations of the focus sensing optical train of FIG. 4A and a cylindrical lens having an effective focal length of 1000 mm.

FIG. 5 shows the shapes for images expected for various focus deviations of the focus sensing optical train of FIG. 4A. At optimal focus (0 µm defocus) a round image is produced as shown in the middle panel. Increasing degrees of negative defocus produce a vertically oblong shape, for example, with a narrow oblong shown for −128 µm defocus and a wider vertical oblong shape for −256 µm defocus. Increasing degrees of positive defocus produce a horizontally oblong shape, for example, with a narrow horizontal oblong shown for +128 µm defocus and a wider horizontal oblong shape for +256 μm defocus. The simulations were performed in Zemax OpticStudio 19.8 and the results had a merit function of 0.001209.

Figure 6A:
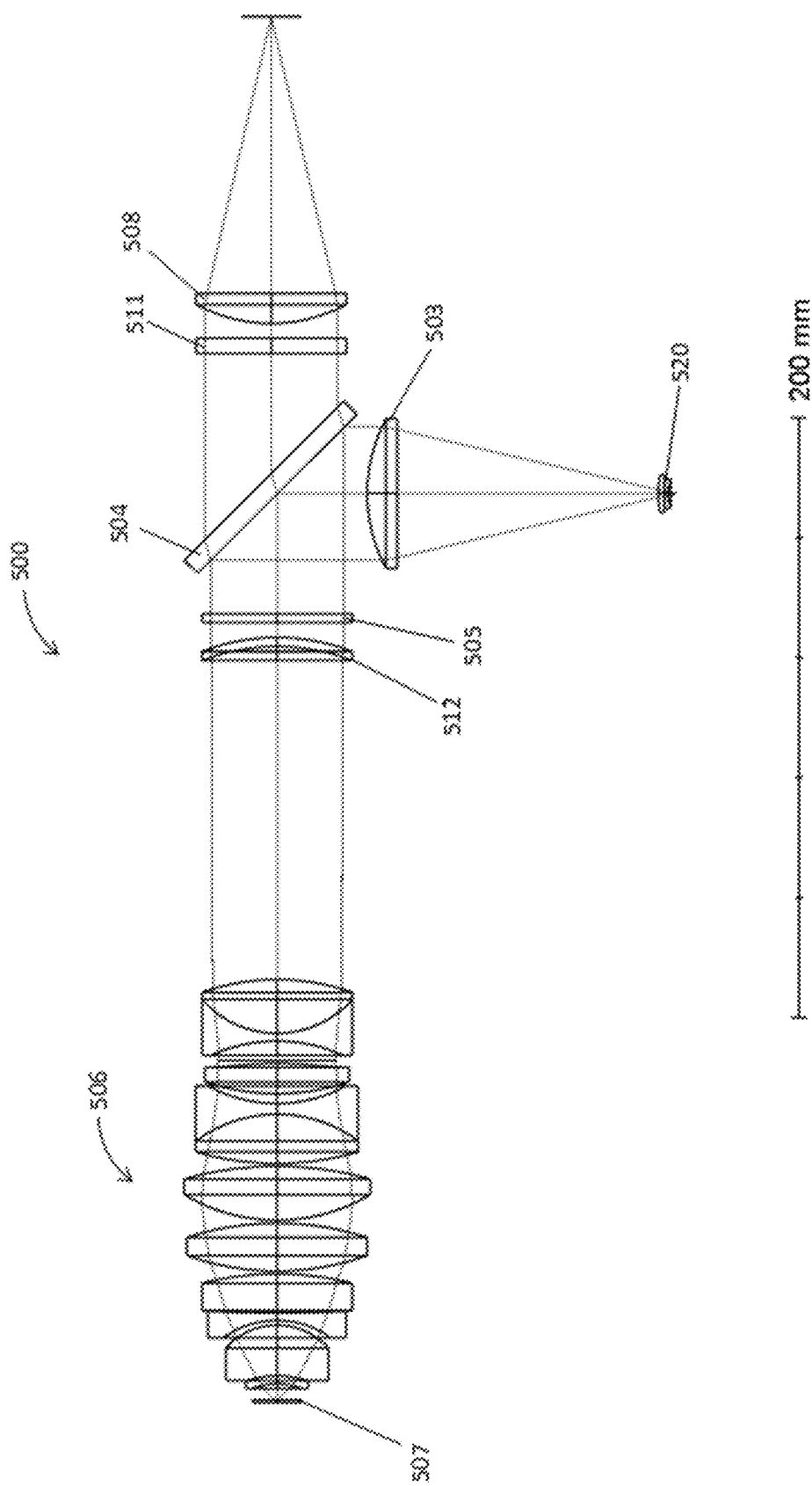
FIG. 6A shows a diagrammatic representation of a focus sensing optical train having a crossed cylindrical lens pair as an astigmatic element.
Figure 6B:
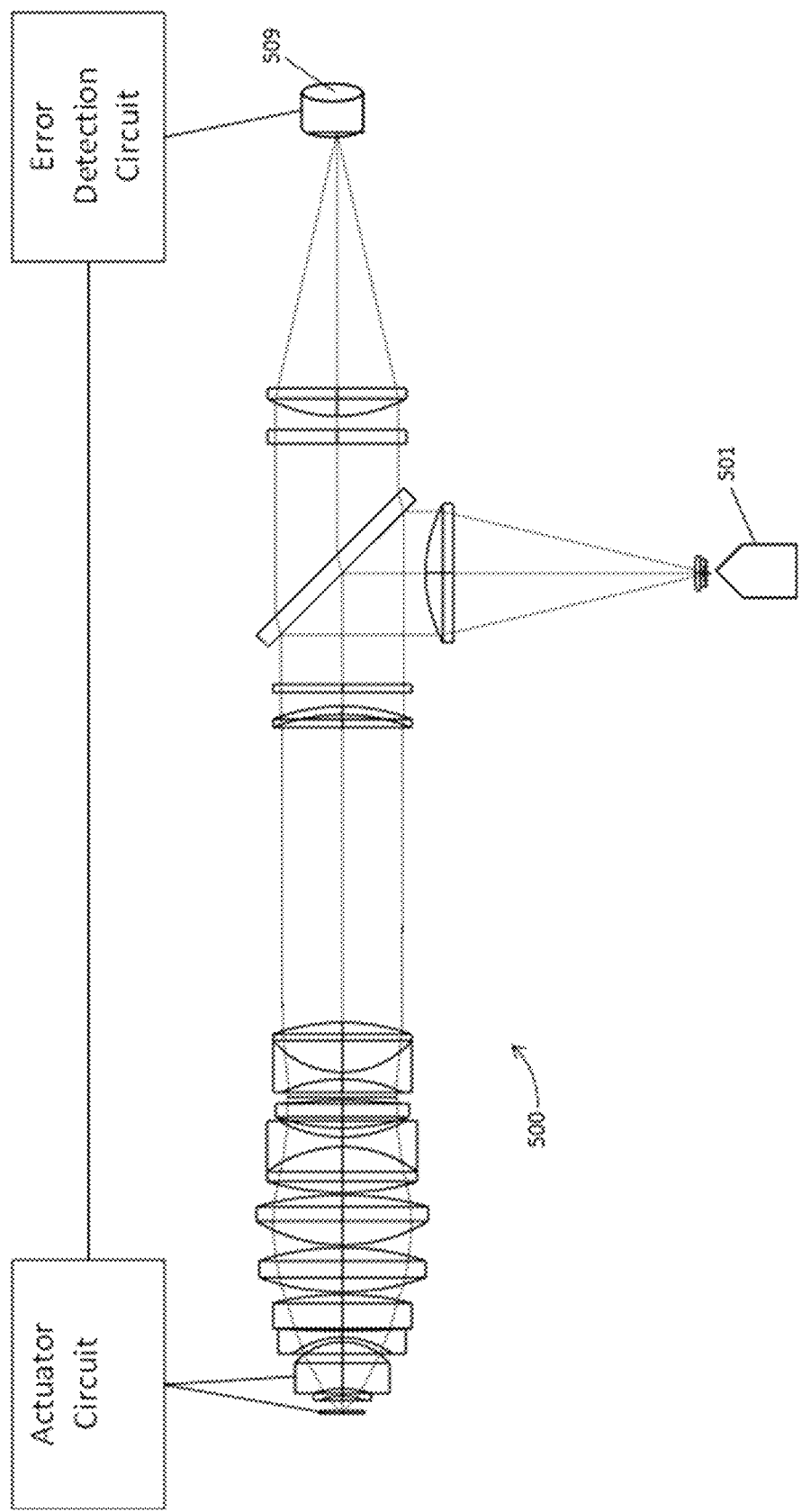
FIG. 6B shows a diagrammatic representation of an autofocus system that includes a focus sensing optical train having a crossed cylindrical lens pair as an astigmatic element.

FIGS. 6A and 6B show an optical train that uses a crossed cylindrical lens pair to introduce an astigmatism for evaluating autofocus and calibration of the optical train. Calibration can be determined from an image produced by a first path through the optical train 500. More specifically, radiation is produced by radiation source 501 (e.g., an LED) and passes through crossed cylindrical lens pair 520 then through collimator 503 to beam splitter 504 where at least a portion of the radiation is reflected to calibrator 505. Beam splitter 504 does not have a toric surface in this example. A portion of the radiation is reflected by the calibrator 505 such that it passes through beam splitter 504, then through bandpass filter 511 and on to imaging lens 508 then detector 509. The product of this first path is an image on detector 509 that is indicative of the calibration state of the optical train. The first path is an example of a calibration sensing path.

As set forth above, a portion of the radiation that was reflected to the calibrator 505 by beam splitter 504 will be reflected back to the beam splitter 504. Another portion of the radiation that was reflected by the beam splitter 504 will follow a second path, whereby the radiation passes through the calibrator 505 then through compensator 512 to the objective 506, and then to a specimen that is positioned on the stage 507. As such, the second path can be considered to include the path from radiation source 501, through crossed cylindrical lens pair 520 then through collimator 503, reflected by beam splitter 504, through calibrator 505, through objective 506 and to the specimen on stage 507. Radiation from the second path can be reflected by the specimen and the reflected radiation can be transmitted along a third path through the objective 506, through compensator 512, through calibrator 505, through beam splitter 504, through imaging lens 508 to detector 509. The product of this third path is an image on detector 509 that is indicative of the focus state of the optical train. The combined second and third paths function as a focus sensing path.

Figure 7:
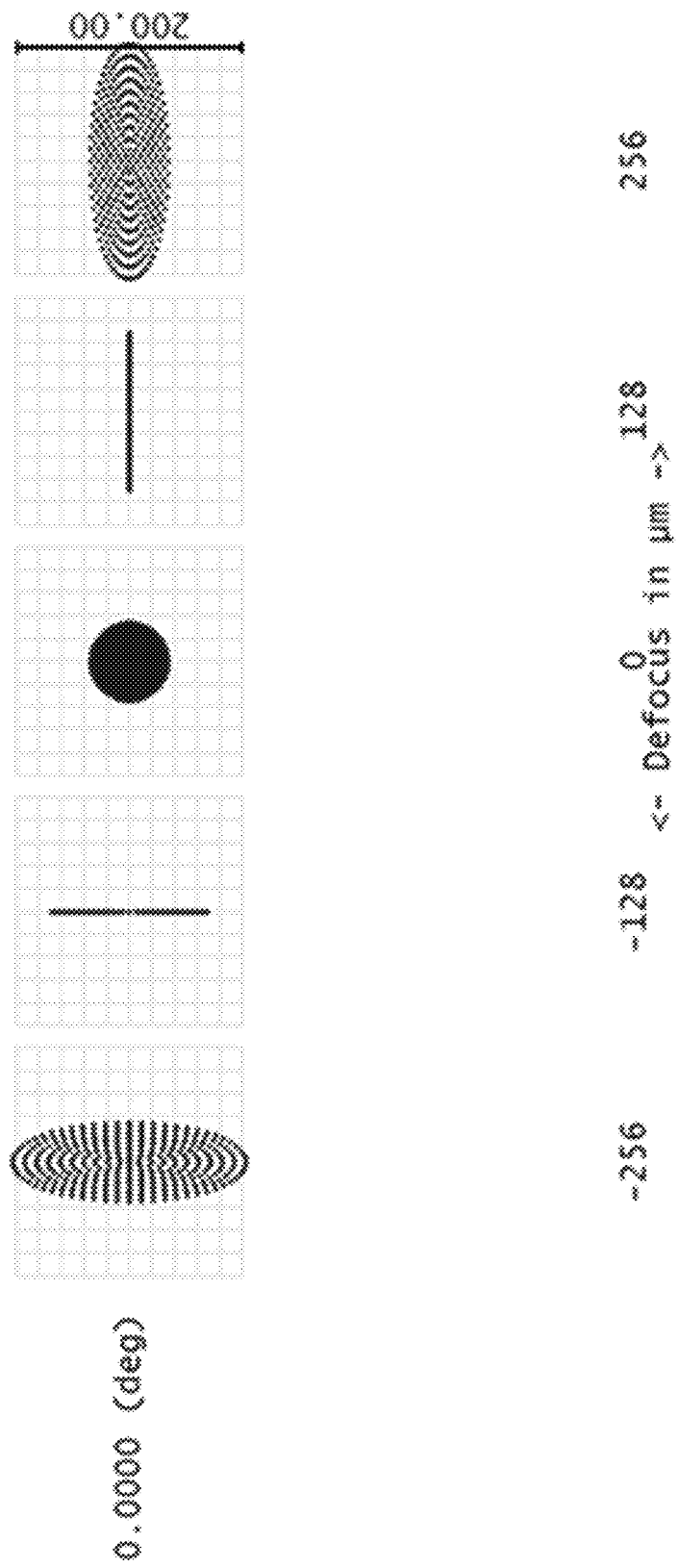
FIG. 7 shows images expected for various focus deviations of the focus sensing optical train of FIG. 6A, wherein the lenses in the crossed cylindrical lens pair have radius of curvature 32.61 and −18.95, respectively.
Figure 8:
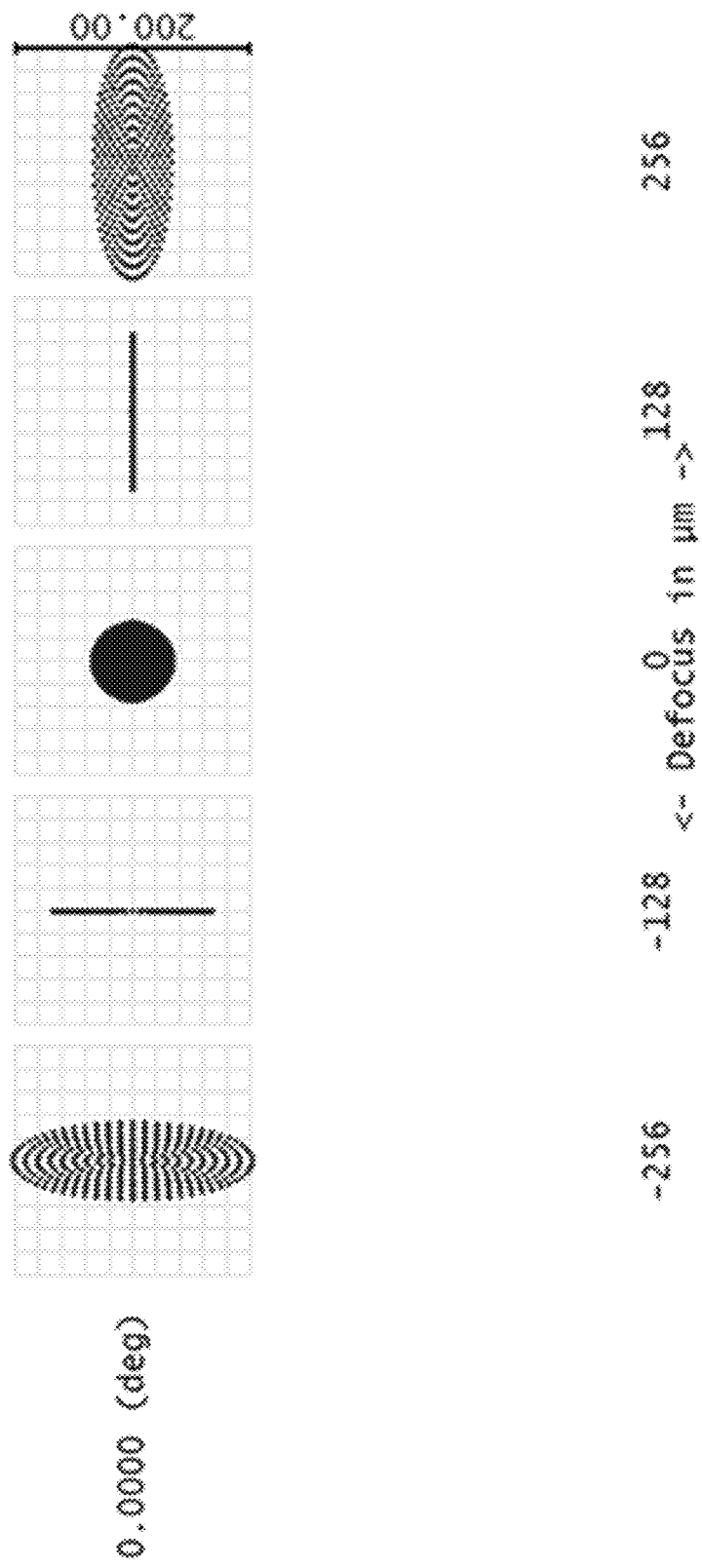
FIG. 8 shows images expected for various focus deviations of the focus sensing optical train of FIG. 6A, wherein the lenses in the crossed cylindrical lens pair have radius of curvature 38.76 and −25.84, respectively.

FIG. 7 and FIG. 8, show the shapes for images expected for various focus deviations of the focus sensing optical train of FIG. 6A. At optimal focus (0 μm defocus) a round image is produced as shown in the middle panel. Increasing degrees of negative defocus produce a vertically oblong shape, for example, with a narrow oblong shown for −128 μm defocus and a wider vertical oblong shape for −256 μm defocus. Increasing degrees of positive defocus produce a horizontally oblong shape, for example, with a narrow horizontal oblong shown for +128 μm defocus and a wider horizontal oblong shape for +256 μm defocus. The simulations were performed in Zemax OpticStudio 19.8. A merit function of 0.000058 resulted when the crossed cylindrical lens pair had radius of curvature of 32.61 and −18.95, respectively (see FIG. 7). A merit function of 0.000276 resulted when the crossed cylindrical lens pair had radius of curvature of 38.76 and −25.84, respectively (see FIG. 8). The simulated results for the optical train having the crossed cylindrical lens pair yielded lower merit functions compared to the simulated results for the optical train having a single cylindrical lens, indicating better quality of the linear focus spot for the former configuration. However, the results indicated that both configurations are useful for determining focus offsets. Any of a variety of collimators can be used in an apparatus of the present disclosure. As exemplified in FIGS. 1A, 3A, 4A and 6A a collimator can function to change diverging light or other radiation from a point source into a parallel beam of rays. The collimator can shape the beam to produce an image having a desired size or shape at a detector. Exemplary collimators include a curved mirror or lens. A collimator can be placed in an optical apparatus such that the source of radiation is at the focus of the collimator. As exemplified above, collimation can occur at a location in an optical train that is upstream of an optical element that introduces an astigmatism. In some configurations, astigmatism can be introduced into an optical train at a location that is upstream of the location where radiation is initially collimated. In other configurations an optical component that collimates radiation can also function to introduce astigmatism. For example, a collimator can have a free form shaped surface that introduces astigmatism.

In the exemplary optical train of FIG. 1A and FIG. 3A, a toric beam splitter performs dual functions of introducing astigmatism into the optics and directing radiation. Astigmatism is introduced via reflection of light off the toric surface of the lens. The beam splitter is placed to direct radiation in two paths. In the first path the beam splitter reflects collimated radiation to the calibration beam splitter. In the second path, the beam splitter transmits radiation from the objective and calibration beam splitter toward the detector. As set forth above, the function of introducing an astigmatism to the optical train can be separated from the function of directing radiation. As such, a beam splitter used in a focus sensing system need not have a toric surface. Examples of optical train configurations that do not use a beam splitter having a toric surface, instead relying upon other astigmatism generators, are provided in FIG. 4 and FIG. 5.

An optical train employed in an apparatus or method for evaluating focus can be configured to produce a signal at a detector that is indicative of the calibration state of at least a subset of the optical elements in the optical train. A calibration beam splitter, or other calibration component, can be placed at a position in an optical train that is diagnostic of the position of the optical components in the train that are upstream of the calibration component. In the examples of FIG. 1A and FIG. 3A, the calibration beam splitter has two functions. The first function is to act as a beam splitter that directs radiation in two paths. In the first path, the calibration beam splitter reflects a portion of the radiation from the toric beam splitter to a detector. In the second path, the calibration beam splitter transmits radiation from the toric beam splitter to the objective and to the specimen. The second function of the calibration component is to provide diagnostic information regarding the calibration state of the optical components in the train that are upstream of the calibration component by directing radiation, via the first path, to a detector where characteristics of the image formed on the detector by the radiation can be used to evaluate any drift from an expected calibration state. It will be understood that a calibration component need not perform both functions. For example, a calibration component can provide the latter function of providing diagnostic information regarding the calibration state of particular optical components without also functioning as a beam splitter.

The calibration component exemplified in FIG. 1 is an optical flat that is placed at a slight angle with respect to the toric beam splitter such that a relatively small fraction of the collimated radiation is reflected back to the detector while a larger fraction of the collimated radiation is transmitted to the specimen via the objective. The calibration component need not be a flat. Rather an optical wedge or other known beam splitter can be used. A similar calibration component can be used in the optical trains shown in FIGS. 3A, 4A and 6A.

Any of a variety of optical elements can serve as an objective in an apparatus or method of the present disclosure including, for example, a lens, mirror, fiber optic, fiber bundle, lens array or other optical element that gathers radiation from a specimen being observed, whether or not the optical element is also capable of focusing the radiation. Particularly useful objectives are described above in the context of FIG. 3A or set forth in U.S. Pat. No. 10,656,368, which is incorporated herein by reference. Objectives or other optical components used in an apparatus or method set forth herein can be configured to transmit radiation in a variety of spectral ranges that are compatible with the optical train that is in use including, but not limited to X-ray, ultraviolet (UV), visible (VIS), infrared (IR), microwave and/or radio wave ranges.

An objective that is used in an apparatus set forth herein can be placed to direct radiation from a specimen such as a surface in or on a vessel. In particular embodiments, an objective, and other optional components of an optical system, can be configured for epi-detection (e.g. epiluminescence or epireflection), whereby radiation is directed from a radiation source, through the objective, to an external or internal surface of a vessel; and whereby luminescence emission or reflection from the surface is directed back through the objective. Alternatively, objectives, and other optional components of an optical system, can be configured for trans-illumination, whereby illumination radiation is directed from an irradiation train to a surface of a vessel wall; and whereby reflection or emission from the surface is directed opposite the direction of the irradiation train and to a detector. Other useful configurations for fluorescence detection include those that excite a vessel via total internal reflection fluorescence (TIRF) or via waveguides.

Particularly useful objectives will have a numerical aperture (NA) that is at least 0.1 and at most 0.9. For example, NA can be between 0.5 and 0.9 or between 0.7 and 0.9. Numerical apertures above 0.95 can be achieved using an immersion objective. An objective or other transmitter can be configured to operate with a detection system that resolves features (e.g. nucleic acid sites) on a surface that are separated by less than 100 microns, 50 microns, 10 microns, 5 microns, 1 micron, or 0.5 micron. The detection system, including objective or other transmitter, can be configured to resolve features having an average area that is smaller than about 1 mm$^2$, 500 µm$^2$, 100 µm$^2$, 25 µm$^2$, 10 m$^2$, 5 µm$^2$, 1 µm$^2$, 500 nm$^2$, or 100 nm$^2$.

An optical system used in an apparatus or method set forth herein can have a field of view that is at least 0.1 mm$^2$, 0.5 mm$^2$, 1 mm$^2$, 2 mm$^2$, 4 mm$^2$, 8 mm$^2$, 12 mm$^2$ or higher. Alternatively and/or additionally, the field of view can be configured to be at most 12 mm$^2$, 8 mm$^2$, 4 mm$^2$, 2 mm$^2$, 1 mm$^2$, 0.5 mm$^2$, 0.1 mm$^2$, or less.

A focus sensing apparatus of the present disclosure can include any of a variety of detectors. In some configurations, the detector is a single camera and both a calibration sensing image and a focus sensing image are formed on the camera. For example, a camera can have two detection areas and each detection area can optionally be assigned to four quadrants. As such, a first image that is formed from a focus sensing optical path can be formed on one of the quadrant areas and a second image that is formed from a calibration sensing path can be formed on the second quadrant area. It will be understood that radiation derived from a focus sensing path need not be detected in the form of an image on a camera. Alternatively or additionally, radiation derived from a calibration radiation path need not be detected in the form of an image on a camera. Other types of detection devices can also be configured to detect radiation derived from a focus sensing path and from a calibration sensing path.

In some configurations, a detector that is used in a focus sensing apparatus can include separate cameras that each detect one of: the radiation derived from a focus sensing path or the radiation derived from a calibration sensing path. Other types of detection devices, besides cameras, can be configured to detect radiation derived from one or both of the paths.

Useful detectors for evaluating focus or for analytical detection of specimens can optionally include photodiodes or cameras. Cameras can have a desired number of pixels to distinguishably detect z-focus state and calibration state for an optical system. For example, a quadrant detector can include at least four pixels (i.e. 1 pixel per quadrant). Generally, it will be preferred to utilize multiple pixels per quadrant to increase accuracy and sensitivity of focus sensing. Rapid readout rates of a camera or other detector are desirable to increase the rate of focus determination and adjustment to suit analytical methods that benefit from rapid detection. For example, the transfer rate from a camera can be 10 MHz or higher, for example 20 or 30 MHz. Other useful detectors include, but are not limited to, an optical quadrant photodiode detector, such as those having a 2×2 array of individual photodiode active areas fabricated on a single chip, examples of which are available from Pacific Silicon Sensor (Westlake Village, Calif.), or a position sensitive detector such as those having a monolithic PIN photodiode with a uniform resistance in one or two dimensions, examples of which are available from Hamamatsu Photonics, K.K., (Hamamatsu City, Japan).

In some configurations it may be useful to shape, direct or otherwise modify a beam of radiation prior to detection. For example, an imaging lens can be placed upstream of a camera in order to create an image on the camera. As exemplified in FIGS. 1A, 3A, 4A, and 6A, an optical train can include an imaging lens (also referred to as a focusing lens) placed upstream of the detector and downstream of other optical components in the train.

A variety of energy sources can be used to produce radiation for use in an apparatus or method herein. Exemplary energy sources include, but are not limited to, a laser, light emitting diode (LED), filament, light bulb, or lamp. The radiation source can produce collimated radiation or alternatively the radiation can be collimated by optical components placed between the radiation source and other components of an optical train, such as an optical train exemplified herein. In particular configurations, it may be advantageous for the focus sensing component of an analytical detection system to use radiation that is different from and does not interfere with radiation employed by the analytical detection component. For example, the radiation source for a focus sensing component can produce radiation having a wavelength that is different from the wavelength(s) detected by the analytical detection component. By way of more specific example, a focus sensing component can employ infrared radiation while the analytical detection component employs visible or ultraviolet radiation.

An apparatus or method of the present disclosure can employ any of a variety of stages to present a specimen for detection. The stage can be configured to translate the specimen along the focus axis. By convention, the focus axis can be parallel to the z dimension of a Cartesian coordinate system. The stage can also be configured to accommodate specimens of a particular type. For example, the specimen can include any of a variety of vessels that are compatible with optical detection including, but not limited to, a microscope slide, multiwell plate (e.g. microtiter plate), flow cell, petri plate or the like. Optionally, a stage can also be configured to translate a specimen in the x or y direction (the xy plane being orthogonal to the z axis).

Particularly useful stages for translating a vessel or other specimen in x, y or z dimensions are set forth in US Pat. App. Pub. No. US 2019/0055598 or U.S. Pat. App. Ser. Nos. 62/807,934 or Ser. No. 16/796,623, each of which is incorporated herein by reference. Those disclosures provide apparatus and methods that can be used to observe a vessel by translational movement of the vessel relative to a detector. The scanning mechanism that is used to translate the vessel with respect to the detector is decoupled from the mechanism that is used to rotationally register the vessel with respect to the detector. Rotational registration of the vessel with respect to a detector can be achieved by physically contacting the vessel with a reference surface, the reference surface being rotationally fixed with respect to the detector. For example, the vessel can be compressed to the reference surface by a preload. Separately, translation can be achieved by a scan actuator (e.g. a pinion) that interacts directly with another surface of the vessel (e.g. a rack on a flow cell or cartridge that complements the pinion).

Accordingly, a detection system that includes a focus sensing apparatus can include (a) a vessel having a lumen and a wall, wherein the wall has an internal surface and an external surface, wherein the internal surface contacts the lumen; (b) a reference surface that forms a structural loop with a detector; (c) a preload configured to urge the external surface of the vessel to contact an area on the reference surface; (d) a scan actuator configured to slide the vessel along the reference surface in a scan dimension; and (e) a transmitter configured to direct, to the detector, a signal from the internal surface or the lumen, when the external surface of the vessel is urged by the preload to contact the reference surface.

A method for evaluating or adjusting focus of an optical detection system can be included in a method of scanning a vessel, wherein the vessel scanning method includes (a) translating a vessel along a reference surface of a detection apparatus, wherein the vessel comprises a lumen and a wall, wherein the lumen comprises analytes, wherein the reference surface contacts at least a portion of the vessel during the translating, and wherein the reference surface forms a structural loop with a detector; and (b) detecting the analytes at different locations along the vessel using the detector, wherein the vessel is urged to the reference surface by a preload during the detecting, thereby scanning the vessel.

Other useful stages for translation in x, y or z are set forth below, and in the references cited below, in the context of nucleic acid sequencing instruments and platforms.

Figure 1B:
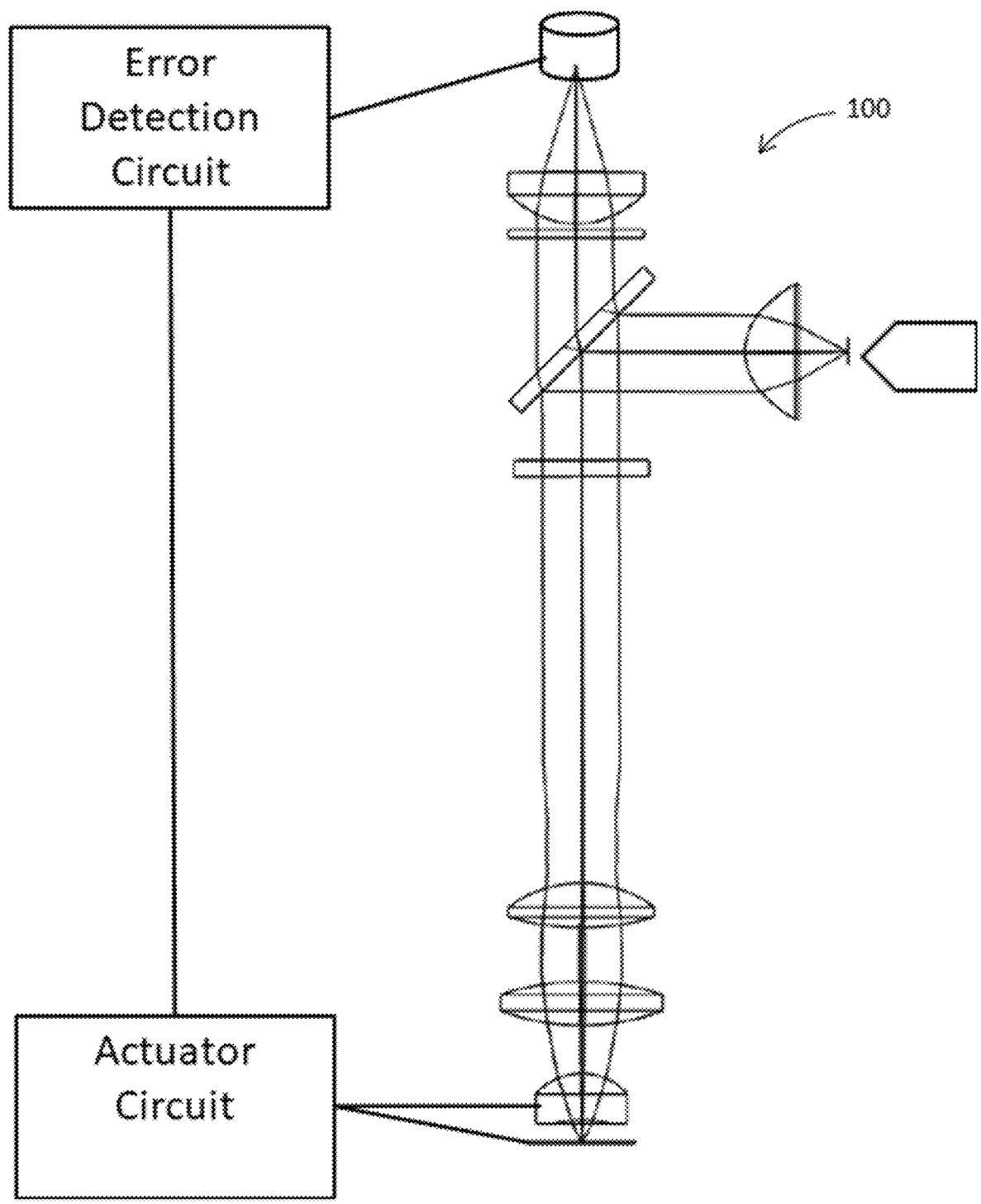
FIG. 1B shows a diagrammatic representation of an autofocus system that includes a focus sensing optical train having a toric beam splitter as an astigmatic element.
Figure 3B:
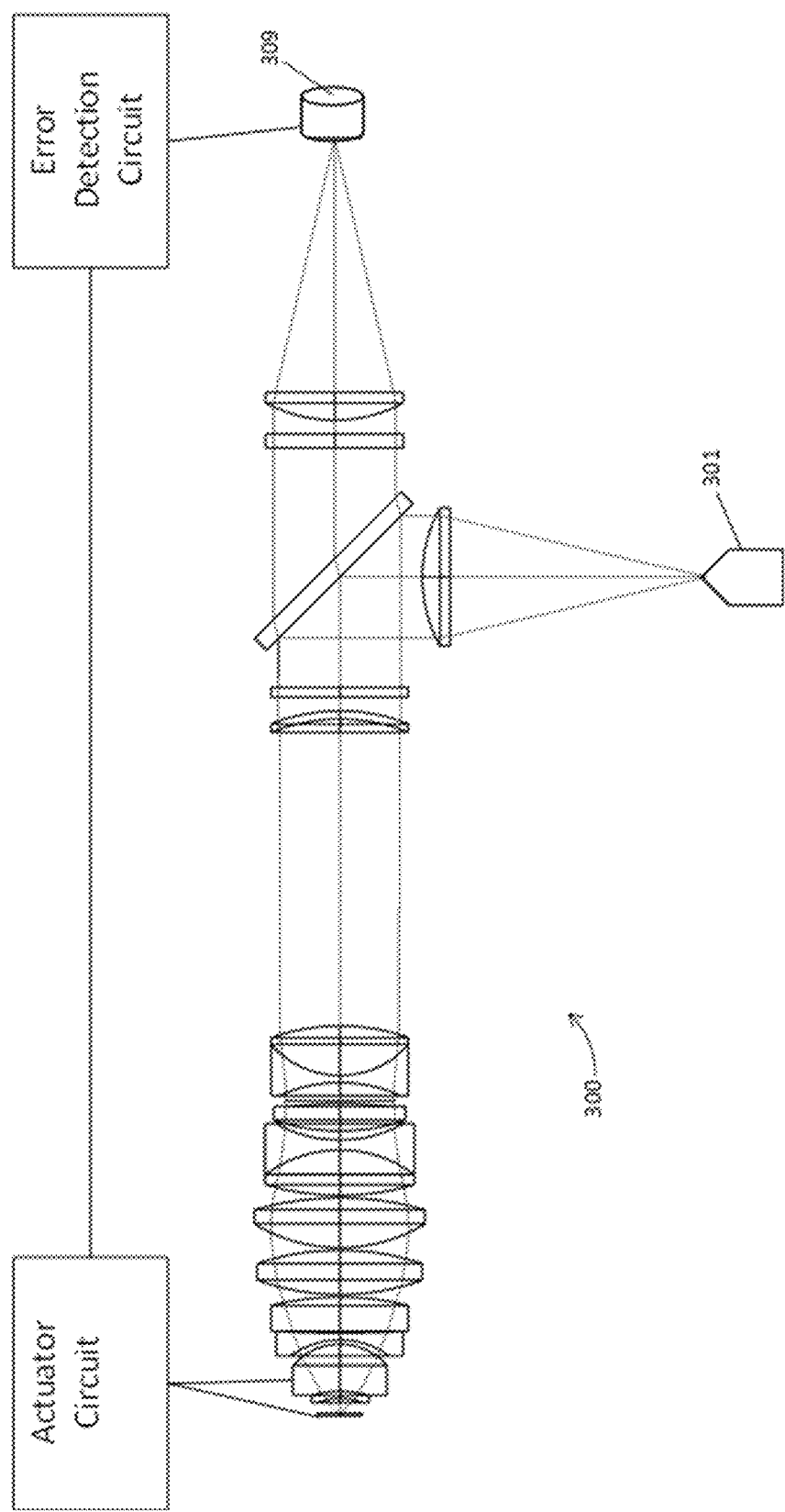
FIG. 3B shows a diagrammatic representation of an autofocus system that includes a focus sensing optical train having a toric beam splitter as an astigmatic element.
Figure 3C:
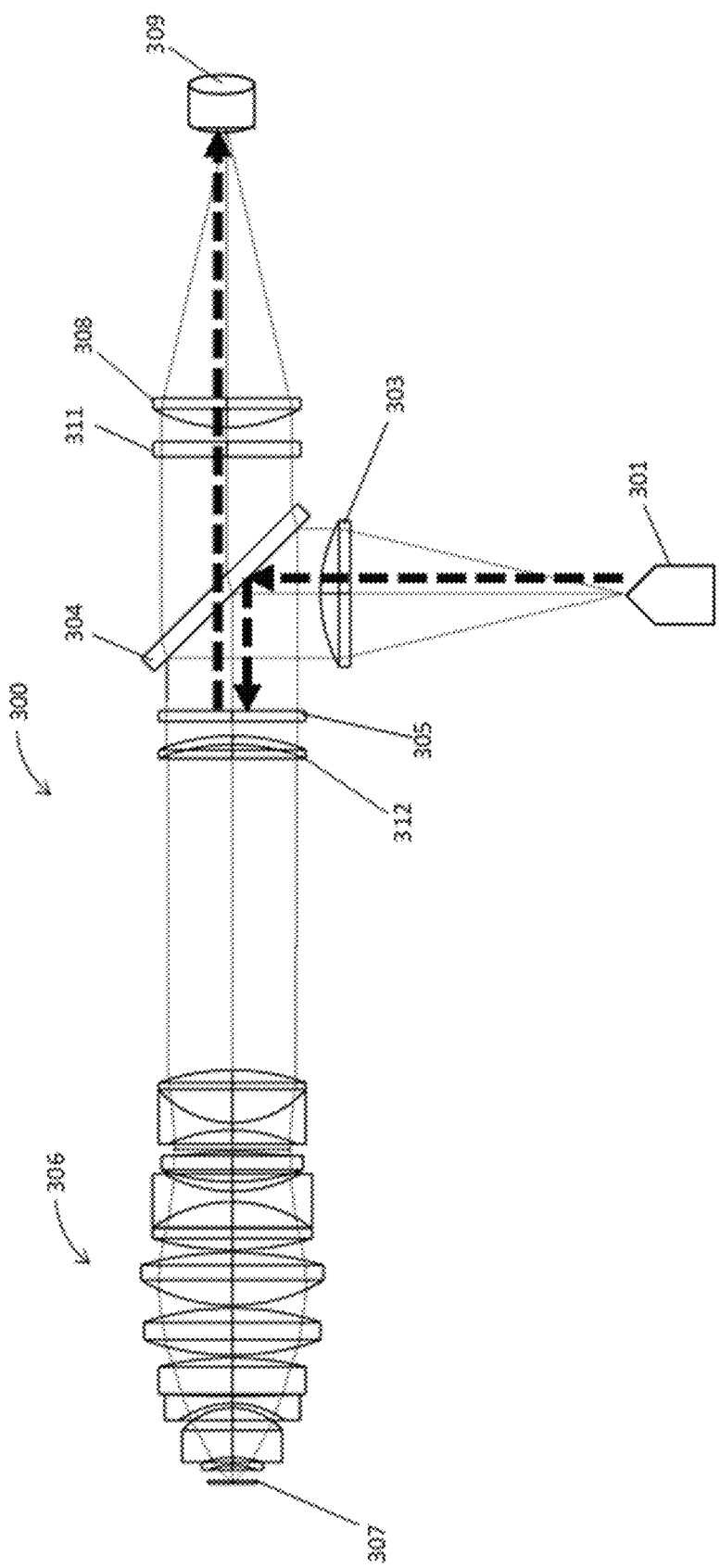
FIG. 3C shows a calibration sensing path.
Figure 3D:
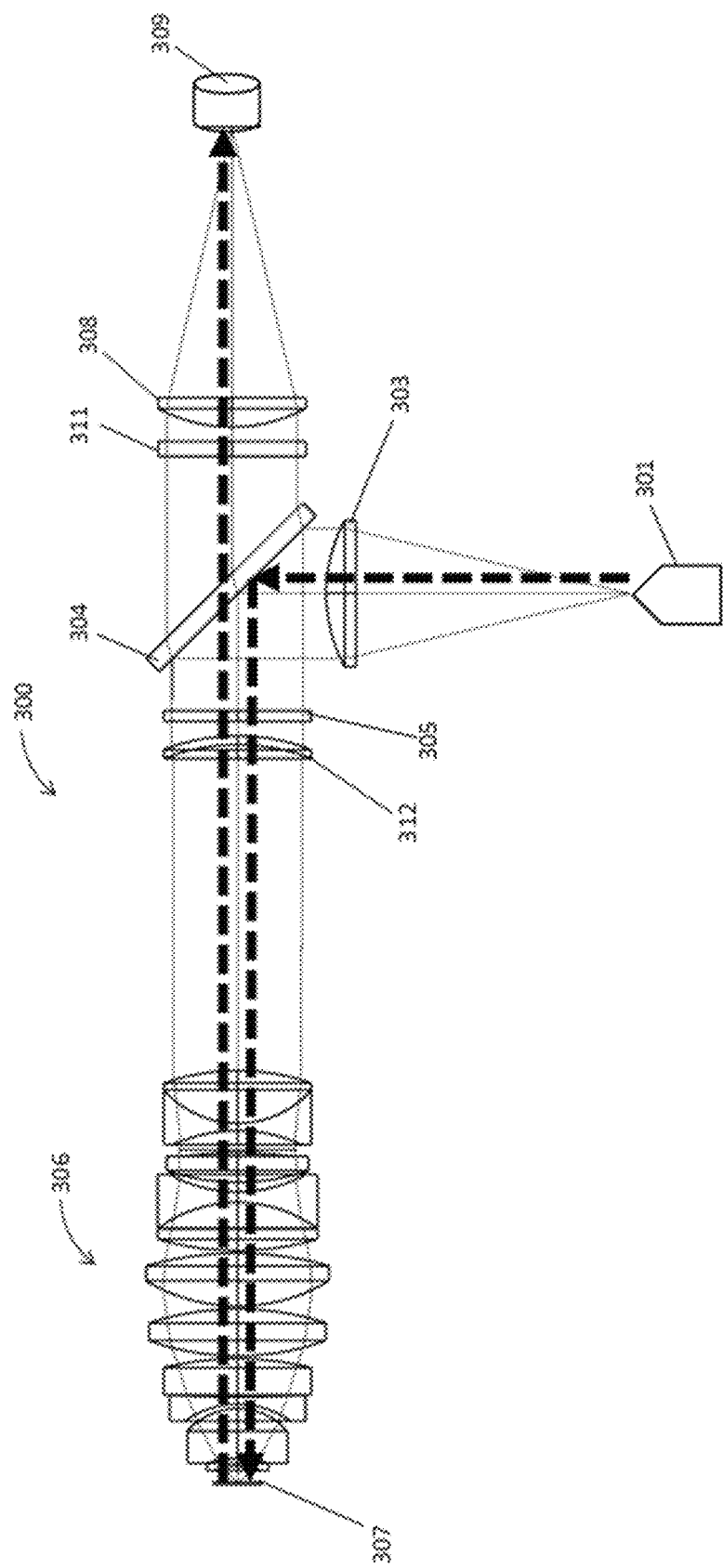
FIG. 3D shows a focus sensing path.
Figure 3E:
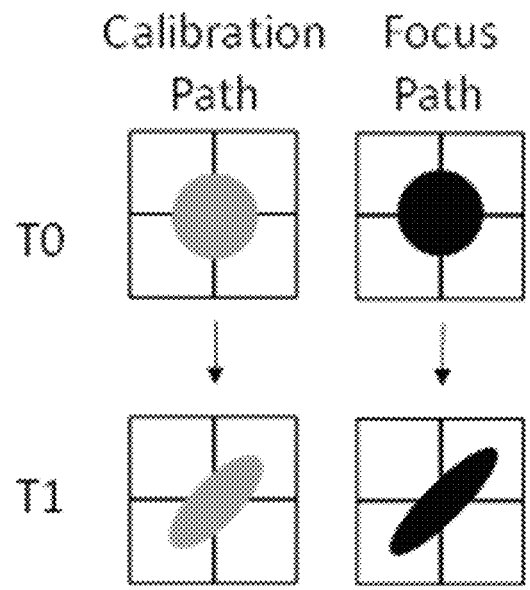
FIG. 3E shows images produced by a calibration sensing path at two different temperatures (grey circle and grey oval) and images produced by a focus sensing path at two different temperatures (black circle and black oval).
Figure 3F:
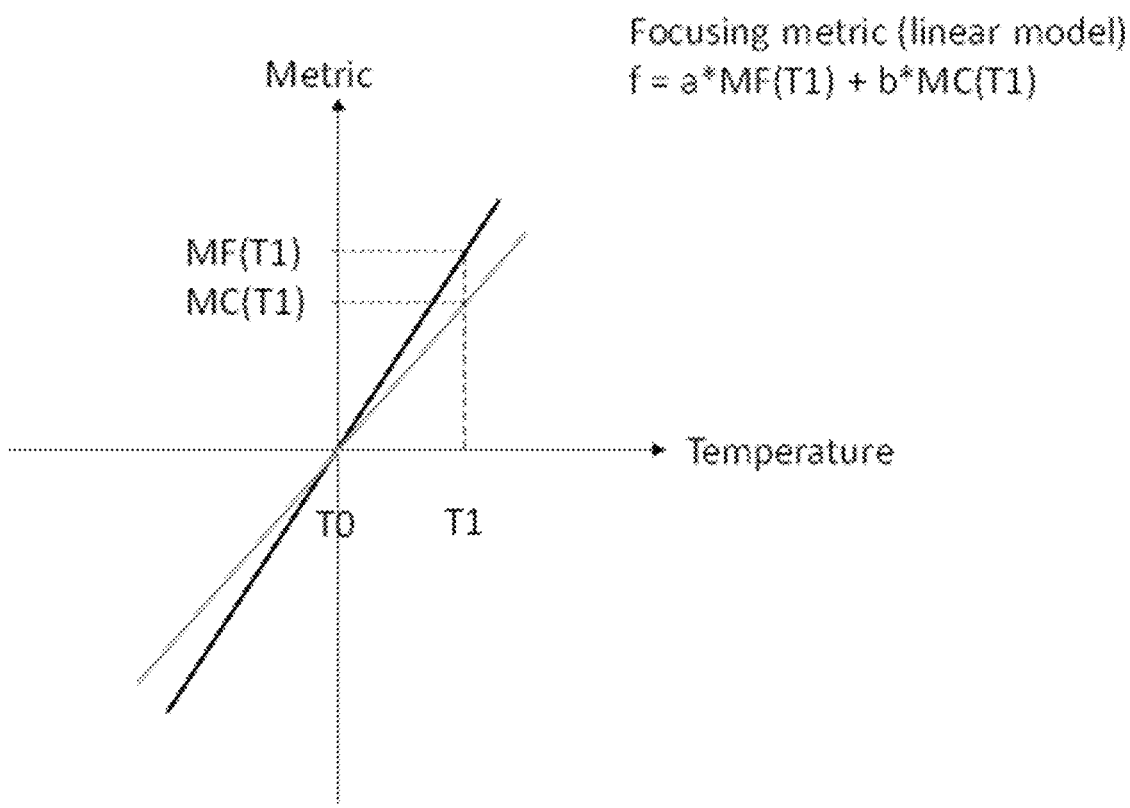
FIG. 3F shows plots of image metric vs. temperature for a calibration sensing path (grey line) and a focus sensing path (black line).

A focus sensing apparatus or method can be a component part of a feedback loop for autofocus adjustment of a detection system. Accordingly, focus adjustment, although capable of being performed manually in response to data communicated to a human user by a focus sensing apparatus or method, can be evaluated in an automated system and used by the automated system to adjust focus in the detection system. FIG. 1B shows a diagrammatic representation of a feedback loop which includes the focus sensing apparatus of FIG. 1A that is in communication with an error detection circuit. The error detection circuit is configured to receive data from the detector 109. The error detection circuit can be configured to determine a calibration state for the optical train 100 from data acquired from a calibration sensing image. Alternatively or additionally, an error detection circuit can be configured to determine a focus state for the optical train 100 from the data for a focus sensing image. The error detection circuit that determines the focus state can be further configured to determine the focus state for the apparatus from not only the data for the focus sensing image but also from the data acquired from the calibration sensing image. In some configurations, the error detection circuit that is used to evaluate data acquired from the calibration sensing image is a separate error detection circuit from the error circuit used to evaluate data acquired from the focus sensing image. Alternatively, the same error detection circuit can be used to evaluate data acquired from the calibration sensing image and data acquired from the focus sensing image. FIGS. 3B, 4B, and 6B show diagrammatic representations of similar error detection circuits for the focus sensing apparatus of FIGS. 3A, 4A, and 6A, respectively. These detection circuits can be configured or used as exemplified herein for the error detection circuit of FIG. 1B.

In configurations that employ image-based detection of astigmatic radiation, the data that is evaluated by the error detection circuit can correlate a shape for a calibration sensing image with positional accuracy of optical components in a calibration sensing path and/or through the data that is evaluated by the error detection circuit can correlate a shape for a focus sensing image with the relative distance between the objective and specimen that are in use. It will be understood, that references to calibration sensing images and focus sensing images in the examples above are not intended to be limiting with regard to the type of data evaluated. Rather, non-image data can be evaluated by an error detection circuit to achieve similar results.

Any of a variety of hardware or software circuits can be used as an error detection circuit. In various configurations, the error detection circuit can be implemented using hardware, machine-readable instructions or algorithm, or a combination thereof. For example, in some implementations the controller can include one or more computer processing units (CPUs), optionally with associated memory. As another example, the circuit can include one or more of the following: field programmable gate array (FPGA), application specific integrated circuit (ASIC), programmable logic device (PLD), complex programmable logic device (CPLD), a programmable logic array (PLA), programmable array logic (PAL) or other similar processing device or circuitry. Optionally, the error detection circuit can include a combination of more than one of the above-identified circuit types.

An error detection circuit can be implemented on the same or different hardware that controls other components of a system that includes a focus sensing apparatus, for example, to acquire, store and process signals for analytical evaluation. In particular embodiments, hardware that includes an error detection circuit can also be used to determine the identity of a nucleotide that is present at a particular location in a template nucleic acid, for example, as part of a sequencing method.

A useful CPU can include, for example, one or more of a personal computer system, server computer system, thin client, thick client, hand-held or laptop device, multiprocessor system, microprocessor-based system, set top box, programmable consumer electronic, network PC, minicomputer system, mainframe computer system, smart phone, or distributed cloud computing environment that includes any of the above systems or devices. The CPU can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The CPU may also include a variety of computer system readable media. Such media may be any available media that is accessible by a cloud computing environment, such as volatile and non-volatile media, and removable and non-removable media.

The memory architecture may include at least one program product having at least one program module implemented as executable instructions that are configured to control one or more component of an apparatus set forth herein or to carry out one or more portions of a method set forth herein. For example, executable instructions may include an operating system, one or more application programs, other program modules, and program data. Generally, program modules may include routines, programs, objects, components, logic, data structures, and so on, that perform particular tasks such as processing of signals detected in a method set forth herein, evaluating focus error and/or evaluating calibration state for an optical train.

An error detection circuit can optionally communicate with one or more external devices such as a keyboard, a pointing device (e.g. a mouse), a display, such as a graphical user interface (GUI), or other device that facilitates interaction of a user with an optical system. Similarly, the error detection circuit can communicate with other devices (e.g., via network card, modem, etc.). For example, an error detection circuit can communicate with an actuator circuit that moves a stage along the focus axis in response to instructions received from the error detection circuit. Such communication can occur via I/O interfaces. Furthermore, an error detection circuit of a system herein may communicate with one or more networks such as a local area network (LAN), a general wide area network (WAN), and/or a public network (e.g., the Internet) via a suitable network adapter.

Continuing with the diagrammatic example in FIG. 1B, an autofocus feedback loop can further include an actuator circuit that is configured to take instructions from the error detection circuit and to adjust the relative position of the objective and specimen along the focus axis. In some configurations the z actuator can be configured to move the stage closer to, or further from, the objective. Alternatively or additionally, the z actuator can be configured to move the objective closer to, or further from, the stage. In some configurations, other optical components of the optical train can be moved to alter focus. For example, the radiation source or the detector can be moved. Generally, it is desirable to move an optical component that is shared by both the focus sensing optical train and the analytical optical train. As such, it is desirable that the optical component that is adjusted be a component through which both the focus sensing optical train and the analytical optical train pass. The feedback loops exemplified in FIGS. 3B, 4B and 6B can be configured or used as exemplified herein for the error detection circuit of FIG. 1B.

Figure 9:
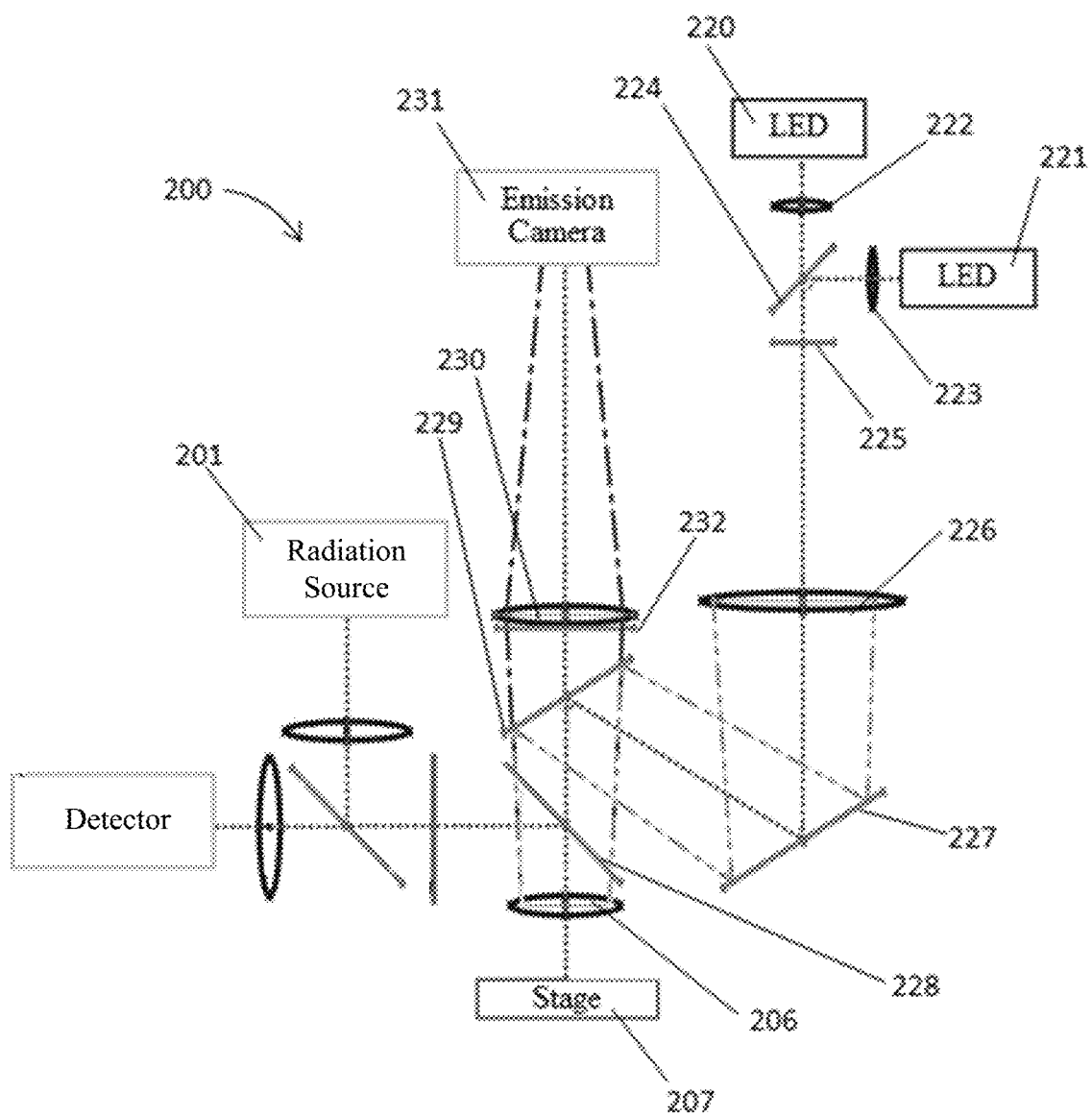
FIG. 9 shows a diagrammatic representation of an epiluminescence detection system having a calibrated focus sensing optical train, a luminescence excitation optical train and a luminescence detection optical train.

A focus sensing apparatus or method set forth herein can be used with any of a variety of analytical optical detection systems. FIG. 9 shows an exemplary optical system 200 that includes an analytical optical train that is integrated with a focus sensing optical train. The optical system 200 comprises a radiation source 201. The analytical optical train and the focus sensing optical train both include objective 206 and as such both optical trains are configured to view a specimen on the stage 207. The focus sensing optical train includes optical elements shown in FIG. 1A, with the addition of focus dichroic 228. The optical train of FIG. 1A can be replaced with one of the optical trains shown in FIGS. 3A, 4A, or 6A, in some configurations. Focus dichroic 228 is configured to reflect radiation between the objective 206 and other components of the focus sensing optical train. Focus dichroic 228 is also configured to transmit radiation between the objective 206 and other components of the analytical optical train. Thus, focus dichroic 228 provides a function of being an intersection or integration point for the analytical optical train and the focus sensing optical train. It will be understood that other optical elements can perform this intersection and integration function as desired to suit a particular layout that achieves a function or provides an advantage set forth herein.

Continuing with the exemplary layout shown in FIG. 9, the analytical optical train is configured for epiluminescence, wherein excitation radiation that excites a specimen and emission signals produced by the excited state specimen transmit through an objective 206 (sometimes referred to as a common objective). Because the focus sensing optical train also transmits to and from the specimen via the objective 206, the focus errors detected for the system can be related to both the accuracy of detecting luminescence signals from a specimen and the accuracy of exciting a particular focal plane of the specimen. When using optical systems that do not include an excitation path, or that excite a specimen via a fluorescence transmission arrangement that does not utilize epi-illumination, a fluorescence evaluation apparatus can be configured to share an objective with one of the emission optical path or excitation optical path, depending upon which path is to be evaluated for focus.

The excitation system of FIG. 9 is configured to excite a specimen at two different wavelengths. A first LED 220 produces excitation radiation at a first wavelength and a second LED 221 produces excitation radiation at a second wavelength. The excitation radiation from the first LED 220 and the second LED 221 is transmitted by condenser lens 222 and condenser lens 223, respectively, to excitation combiner 224 which converges the two excitation paths. The excitation paths then pass through dual band pass filter 225 and excitation lens 226 to reflector 227, which in turn reflects the excitation radiation to excitation dichroic 229. The excitation radiation is reflected by excitation dichroic 229 then passes through focus dichroic 228 to objective 206 and to a specimen on stage 207.

The exemplary system in FIG. 9 includes two excitation sources. It will be understood, that a similar system can be modified for use with only 1 excitation source or with greater than 2 excitation sources. For example, including up to four excitation sources can be beneficial for applications that distinguish 4 different nucleotide types that may be present in a nucleic acid based on each being labeled with one of four different luminophores that are distinguished based on different responses to different excitation wavelengths.

The analytical optical train also includes optical components that direct luminescent signals from the specimen on stage 207 to emission camera 231. Emitted radiation from the specimen can be collected by objective 206 and transmitted through focus dichroic 228, then through excitation dichroic 229, then through emission dual bandpass 232 and imaging tube 230 to emission camera 231. In this exemplary configuration, emission from luminophores excited at two wavelengths can be detected by a single camera. The system can be readily modified to include two or more cameras by introducing splitting optic into the emission detection path. For example, a system can include up to four different cameras to distinguish labels for four different nucleotide types when detecting nucleic acids.

Several aspects of calibrated focus sensing have been exemplified herein with regard to detection of astigmatic radiation. It will be understood, that other properties of radiation can provide a basis for evaluating focus and calibration of an optical system. For example, a focus sensing apparatus can be configured with an optical train that transmits polarized light in a way that changes in optical train will manifest as observable changes in polarization of the light that can, in turn be correlated with focus position and calibration of the focus apparatus. More specifically, the optical path of FIG. 1 can be modified as follows. Toric beam splitter 104 can be replaced with a polarizing beam splitter that reflects radiation of one polarization and transmits radiation of a second polarization. The radiation source can be a source of unpolarized radiation (e.g. an LED) or a laser oriented to have two polarizations. Continuing with the modified optical path, a polarization rotator can be added to the optical train to convert polarization from the transmitted polarization state to the reflected polarization state. A second polarization rotator can be added to the sensing arm of the optical path to convert polarization for the transmitted radiation through the polarization beam splitter to the detector.

In particular configurations, a focus sensing apparatus or method set forth herein can employ optical sub-systems or components used in nucleic acid sequencing systems. Several such detection apparatus are configured for optical detection, for example, detection of fluorescent signals. Examples of detection apparatus and components thereof that can be used to detect a vessel herein are described, for example, in US Pat. App. Pub. No. 2010/0111768 A1 or U.S. Pat. Nos. 7,329,860; 8,951,781 or 9,193,996, each of which is incorporated herein by reference. Other detection apparatus include those commercialized for nucleic acid sequencing such as those provided by Illumina™, Inc. (e.g. HiSeq™, MiSeq™, NextSeq™, or NovaSeq™ systems), Life Technologies™ (e.g. ABI PRISM™, or SOLiD™ systems), Pacific Biosciences (e.g. systems using SMRT™ Technology such as the Sequel™ or RS II™ systems), or Qiagen (e.g. Genereader™ system). Other useful detectors are described in U.S. Pat. Nos. 5,888,737; 6,175,002; 5,695,934; 6,140,489; or 5,863,722; or US Pat. Pub. Nos. 2007/007991 A1, 2009/0247414 A1, or 2010/0111768; or WO2007/123744, each of which is incorporated herein by reference in its entirety. In particular embodiments, the autofocus system of a known sequencing system can be replaced with a focus sensing apparatus set forth herein.

Accordingly, the present disclosure provides a nucleic acid sequencing system that includes (a) a stage configured to hold a specimen; (b) an optical train including a radiation source, calibration optic, objective and detector, the optical train forming a first path wherein radiation from the radiation source is directed to the calibration optic and then a first portion of the radiation is directed to the detector, thereby forming a first image on the detector, wherein a second portion of the radiation follows a second path from the calibration optic then through the objective to the specimen, wherein the optical train forms a third path wherein radiation reflected from the specimen is transmitted through the objective, then to the detector, thereby forming a second image on the detector, and wherein the radiation that forms the first image is astigmatic; and (c) a luminescence optical train for directing radiation from an excitation radiation source through the objective to the specimen and for directing luminescent emission radiation from the specimen through the objective to a luminescence detector.

In particular configurations, a nucleic acid sequencing system can include (a) a stage configured to hold a specimen; (b) an optical train comprising a radiation source, collimator, primary beam splitter, calibration beam splitter, objective and detector, the optical train forming a first path wherein radiation from the radiation source is collimated by the collimator, then transmitted to the primary beam splitter, then to the calibration beam splitter, then a first portion of the radiation continues on the first path from the calibration beam splitter to the primary beam splitter, then to the detector, thereby forming a first image on the detector, wherein a second portion of the radiation follows a second path from the calibration beam splitter then through the objective to the specimen, wherein the optical train forms a third path wherein radiation from the specimen is transmitted through the objective, then through the calibration beam splitter, then through the primary beam splitter, then to the detector, thereby forming a second image on the detector, and wherein the optical train comprises an astigmatism generator between the radiation source and the calibration beam splitter; and (c) a luminescence optical train for directing radiation from an excitation radiation source through the objective to the specimen and for directing luminescent emission radiation from the specimen through the objective to a luminescence detector. Optionally, the astigmatism generator is a toric surface of the primary beam splitter, the toric surface configured for transmitting radiation from the collimator to the calibration beam splitter. In another option, the astigmatism generator is an astigmatic lens, such as a cylindrical lens or a crossed cylindrical lens pair, positioned between the radiation source and the calibration beam splitter in the optical train.

A sequencing system or other detection system can be configured to have a radiation source that is used for both a focus sensing optical train and an analytical optical train. Accordingly, the radiation source can be used to produce both a reflection that is used for focus sensing and to produce luminescence emission for analytical analysis of the specimen being focused. Alternatively, separate radiation sources can be used, one for a focus sensing optical train (e.g. to produce a reflection that is evaluated to determine focus), and another for an analytical optical train (e.g. to excite luminophores that produce luminescent emission used for analysis of a specimen).

A sequencing system or other detection system can be configured to have a detector that is used for both focus sensing of a specimen and for analytical evaluation of the specimen. Accordingly, the detector can be used to detect both a reflection that is used for focus sensing and to detect luminescence emission for analytical analysis of the specimen being focused. Alternatively, separate detectors can be used, one for a focus sensing optical train (e.g. to observe a reflection that is evaluated to determine focus), and another for an analytical optical train (e.g. to observe emission from luminophores that indicate a characteristic of interest for a specimen).

Any of a variety of vessels can be used in an apparatus or method set forth herein. A flow cell can be useful, especially for nucleic acid sequencing applications or other applications that utilize repeated reagent deliveries. A flow cell can include a solid support to which one or more target analytes or reagents are attached. A particularly useful solid support (whether used in a flow cell or other vessel) is one having an array of sites. Arrays provide the advantage of facilitating multiplex detection. For example, different reagents or analytes (e.g. cells, nucleic acids, proteins, candidate small molecule therapeutics etc.) can be attached to an array via linkage of each different analyte to a particular site of the array. Exemplary array substrates that can be useful include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Further examples of commercially available array substrates that can be used include, for example, an Affymetrix GeneChip™ array. A spotted array substrate can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful array substrates include those that are used in nucleic acid sequencing applications. For example, arrays that are used to create attached amplicons of genomic fragments (often referred to as clusters) can be particularly useful. Examples of substrates that can be modified for use for sequencing or other applications set forth herein or known in the art include those described in Bentley et al., *Nature* 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082 A1, each of which is incorporated herein by reference.

An array can have sites that are separated by less than 100 µm, 50 µm, 10 µm, 5 µm, 1 µm, or 0.5 µm. In particular embodiments, sites of an array can each have an area that is larger than about 100 nm$^2$, 250 nm$^2$, 500 nm$^2$, 1 µm$^2$, 2.5 µm$^2$, 5 µm$^2$, 10 µm$^2$, 100 µm$^2$, or 500 µm$^2$. Alternatively or additionally, sites of an array can each have an area that is smaller than about 1 mm$^2$, 500 µm$^2$, 100 µm$^2$, 25 µm$^2$, 10 µm$^2$, 5 µm$^2$, 1 µm$^2$, 500 nm$^2$, or 100 nm$^2$. Indeed, a site can have a size that is in a range between an upper and lower limit selected from those exemplified above. An array can have sites at any of a variety of densities including, for example, at least about 10 sites/cm$^2$, 100 sites/cm$^2$, 500 sites/cm$^2$, 1,000 sites/cm$^2$, 5,000 sites/cm$^2$, 10,000 sites/cm$^2$, 50,000 sites/cm$^2$, 100,000 sites/cm$^2$, 1,000,000 sites/cm$^2$, 5,000,000 sites/cm$^2$, or higher. An embodiment of the apparatus or methods set forth herein can be used to image an array at a resolution sufficient to distinguish sites at the above densities or site separations.

Several embodiments utilize optical detection of analytes in a flow cell. Accordingly, a flow cell can include one or more channels each having at least one transparent window. In particular embodiments, the window can be transparent to radiation in a particular spectral range including, but not limited to x-ray, ultraviolet (UV), visible (VIS), infrared (IR), microwave and/or radio wave radiation. In some cases, analytes are attached to an inner surface of the window(s). Alternatively or additionally, one or more windows can provide a view to an internal substrate to which analytes are attached. Exemplary flow cells and physical features of flow cells that can be useful in a method or apparatus set forth herein are described, for example, in US Pat. App. Pub. No. 2010/0111768 A1, WO 05/065814 or US Pat. App. Pub. No. 2012/0270305 A1, each of which is incorporated herein by reference.

Exemplary reaction vessels (e.g. flow cells) and fluidic components that can be modified, in accordance with teachings herein, for use in combination with detection components of the present disclosure are described in commonly owned US Pat. App. Pub. No. 2018/0280975 A1, which is incorporated herein by reference. Other fluidic components that are useful, particularly for cyclic reactions such as nucleic acid sequencing reactions, are set forth in US Pat. App. Pub. Nos. 2009/0026082 A1; 2009/0127589 A1; 2010/0111768 A1; 2010/0137143 A1; or 2010/0282617 A1; or U.S. Pat. Nos. 7,329,860; 8,951,781 or 9,193,996, each of which is incorporated herein by reference.

As will be evident from the examples set forth herein, a vessel can be open (e.g. a well of a multi-well plate, surface of a chip, or surface of a sheet) or the vessel can be enclosed (e.g. a lane of a flow cell). It will be understood that, wells of a multi-well plate can optionally be covered to create an enclosed vessel and similarly a sheet, belt, tape or ribbon can have multiple layers such that an internal lumen occurs between layers. Alternatively, a vessel can have one or more open structures such as a trough, well or other concave structure that contains a fluid. A vessel can also have a convex or protruding structure such as a post or ridge, and optionally individual protrusions can each be attached to one or more analyte that is to be detected or manipulated.

A detection apparatus or other apparatus of the present disclosure can include a fluidics system for delivering reagents to a vessel that is to be detected. Accordingly, one or more reservoirs can be fluidically connected to an inlet valve of the vessel. The apparatus can further include a pressure supply for driving reagents from reservoirs to the vessel. The apparatus can include a waste reservoir that is fluidically connected to the vessel to remove spent reagents. Taking as an example an embodiment where the vessel is a flow cell, reagents can be delivered via pump to the flow cell through the inlet and then the reagents can flow through the flow cell outlet to a waste reservoir. The reservoirs can include reagents for any of a variety of analytical procedures including, but not limited to nucleic acid sequencing, nucleic acid genotyping, nucleic acid expression analysis, protein sequencing, protein binding analysis (e.g. ELISA), small molecule receptor binding, protein phosphorylation analysis, nucleic acid synthesis or protein synthesis. Alternatively or additionally, the reservoirs can include reagents for a preparative process. Exemplary preparative processes include, but are not limited to, nucleic acid synthesis, peptide synthesis, assembly of oligonucleotides into genes, photolithography, nanofabrication or microfabrication (e.g. via laser etching), laser ablation, or the like.

A fluidic system can include at least one manifold and/or at least one valve for directing reagents from reservoirs to a vessel where detection occurs. Manifolds are particularly useful in sequencing instruments due to the relatively large number of different reagents that are delivered during a sequencing protocol. Exemplary protocols and useful reagents are set forth in further detail below and in references that are incorporated herein by reference. Fluid flow from the reservoirs can be selected via valves such as a solenoid valve (e.g. those made by Takasago Electric, Japan), ball valve, diaphragm valve or rotary valve.

The present disclosure provides apparatus and methods that are particularly useful for performing cyclical reactions due to the speed and accuracy of focus sensing (and if desired, adjustment) provided. Each cycle can include delivering reagents for the reaction to a flow cell or other vessel where, optionally, the reaction, or products of the reaction, will be observed. Each cycle can further include detection of the vessel using apparatus or methods set forth herein. The methods are exemplified herein in the context of a nucleic acid sequencing reaction. However, those skilled in the art will understand from the teaching herein how to modify the methods, and the apparatus, for other cyclical reactions such as nucleic acid synthesis reactions, peptide sequencing reactions, peptide synthesis reactions, combinatorial small molecule synthesis reactions or the like. However, the method need not be cyclical and can instead be carried out in a non-repetitive configuration, for example, to observe a single reaction or phenomenon.

Particularly useful sequencing reactions are Sequencing By Binding™ (SBB™) reactions as described in commonly owned US Pat. App. Pub. Nos. 2017/0022553 A1, 2018/0044727 A1, 2018/0187245 A1 or 2018/0208983 A1, each of which is incorporated herein by reference. Generally, methods for determining the sequence of a template nucleic acid molecule can be based on formation of a ternary complex (between polymerase, primed nucleic acid and cognate nucleotide) under specified conditions. The method can include an examination phase followed by a nucleotide incorporation phase.

The examination phase can be carried out in a flow cell (or other vessel), the flow cell containing at least one template nucleic acid molecule primed with a primer by delivering to the flow cell reagents to form a first reaction mixture. The reaction mixture can include the primed template nucleic acid, a polymerase and at least one nucleotide type. Interaction of polymerase and a nucleotide with the primed template nucleic acid molecule(s) can be observed under conditions where the nucleotide is not covalently added to the primer(s); and the next base in each template nucleic acid can be identified using the observed interaction of the polymerase and nucleotide with the primed template nucleic acid molecule(s). The interaction between the primed template, polymerase and nucleotide can be detected in a variety of schemes. For example, the nucleotides can contain a detectable label. Each nucleotide can have a distinguishable label with respect to other nucleotides. Alternatively, some or all of the different nucleotide types can have the same label and the nucleotide types can be distinguished based on separate deliveries of different nucleotide types to the flow cell. In some embodiments, the polymerase can be labeled. Polymerases that are associated with different nucleotide types can have unique labels that distinguish the type of nucleotide to which they are associated. Alternatively, polymerases can have similar labels and the different nucleotide types can be distinguished based on separate deliveries of different nucleotide types to the flow cell. Detection can be carried out using an apparatus or method set forth herein.

During the examination phase, discrimination between correct and incorrect nucleotides can be facilitated by ternary complex stabilization. A variety of conditions and reagents can be useful. For example, the primer can contain a reversible blocking moiety that prevents covalent attachment of nucleotide; and/or cofactors that are required for extension, such as divalent metal ions, can be absent; and/or inhibitory divalent cations that inhibit polymerase-based primer extension can be present; and/or the polymerase that is present in the examination phase can have a chemical modification and/or mutation that inhibits primer extension; and/or the nucleotides can have chemical modifications that inhibit incorporation, such as 5' modifications that remove or alter the native triphosphate moiety. The examination phase can include focus sensing apparatus and methods set forth herein.

The extension phase can then be carried out by creating conditions in the flow cell where a nucleotide can be added to the primer on each template nucleic acid molecule. In some embodiments, this involves removal of reagents used in the examination phase and replacing them with reagents that facilitate extension. For example, examination reagents can be replaced with a polymerase and nucleotide(s) that are capable of extension. Alternatively, one or more reagents can be added to the examination phase reaction to create extension conditions. For example, catalytic divalent cations can be added to an examination mixture that was deficient in the cations, and/or polymerase inhibitors can be removed or disabled, and/or extension competent nucleotides can be added, and/or a deblocking reagent can be added to render primer(s) extension competent, and/or extension competent polymerase can be added.

It will be understood that any of a variety of nucleic acid sequencing reactions can be carried out using an apparatus and method of the present disclosure. Other exemplary sequencing methods are set forth below.

Sequencing-by-synthesis (SBS) techniques can be used. SBS generally involves the enzymatic extension of a nascent primer through the iterative addition of nucleotides against a template strand to which the primer is hybridized. Briefly, SBS can be initiated by contacting target nucleic acids, attached to sites in a vessel, with one or more labeled nucleotides, DNA polymerase, etc. Those sites where a primer is extended using the target nucleic acid as template will incorporate a labeled nucleotide that can be detected. Detection can employ a focus sensing apparatus or method set forth herein. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the vessel (before or after detection occurs). Washes can be carried out between the various delivery steps. The cycle can be performed n times to extend the primer by n nucleotides, thereby detecting a sequence of length n. Exemplary SBS procedures, reagents and detection components that can be readily adapted for use with a detection apparatus produced by the methods of the present disclosure are described, for example, in Bentley et al., *Nature* 456:53-59 (2008), WO 04/018497; WO 91/06678; WO 07/123744; U.S. Pat. No. 7,057,026; 7,329,492; 7,211,414; 7,315,019 or 7,405,281, and US Pat. App. Pub. No. 2008/0108082 A1, each of which is incorporated herein by reference. Also useful are SBS methods that are commercially available from Illumina, Inc. (San Diego, Calif.).

Other sequencing procedures can be used, such as pyrosequencing. Pyrosequencing detects the release of inorganic pyrophosphate (PPi) as nucleotides are incorporated into a nascent primer hybridized to a template nucleic acid strand (Ronaghi, et al., *Analytical Biochemistry* 242 (1), 84-9 (1996); Ronaghi, *Genome Res.* 11 (1), 3-11 (2001); Ronaghi et al. *Science* 281 (5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system that is configured to focus and/or detect a vessel using apparatus and methods set forth herein.

Sequencing-by-ligation reactions are also useful including, for example, those described in Shendure et al. *Science* 309:1728-1732 (2005); U.S. Pat. No. 5,599,675; or U.S. Pat. No. 5,750,341, each of which is incorporated herein by reference. Some embodiments can include sequencing-by-hybridization procedures as described, for example, in Bains et al., *Journal of Theoretical Biology* 135 (3), 303-7 (1988); Drmanac et al., *Nature Biotechnology* 16, 54-58 (1998); Fodor et al., *Science* 251 (4995), 767-773 (1995); or WO 1989/10977, each of which is incorporated herein by reference. In both sequencing-by-ligation and sequencing-by-hybridization procedures, primers that are hybridized to nucleic acid templates are subjected to repeated cycles of extension by oligonucleotide ligation. Typically, the oligonucleotides are fluorescently labeled and can be detected to determine the sequence of the template, for example, using an apparatus or method set forth herein for focusing and detection.

Steps for the above sequencing methods can be carried out cyclically. For example, examination and extension steps of an SBB™ method can be repeated such that in each cycle a single next correct nucleotide is examined (i.e. the next correct nucleotide being a nucleotide that correctly binds to the nucleotide in a template nucleic acid that is located immediately 5' of the base in the template that is hybridized to the 3'-end of the hybridized primer) and, subsequently, a single next correct nucleotide is added to the primer. Any number of cycles of a sequencing method set forth herein can be carried out including, for example, at least 1, 2, 5, 10, 20, 25, 30, 40, 50, 75, 100, 150 or more cycles. Alternatively or additionally, no more than 150, 100, 75, 50, 40, 30, 25, 20, 10, 5, 2 or 1 cycles are carried out. Focusing can be carried out for some or all of the cycles. In some cases, focusing can occur several times within a cycle. For example, focusing can be carried out prior to acquiring images from each of multiple tiles that are detected during each cycle.

Nucleic acid template(s), to be sequenced, can be added to a vessel using any of a variety of known methods. In some embodiments, a single nucleic acid molecule is to be sequenced. The nucleic acid molecule can be delivered to a vessel and can optionally be attached to a surface in the vessel. In some embodiments, the molecule is subjected to single molecule sequencing. Alternatively, multiple copies of the nucleic acid can be made, and the resulting ensemble can be sequenced. For example, the nucleic acid can be amplified on a surface (e.g. on the inner wall of a flow cell) using techniques set forth in further detail below.

In multiplex embodiments, a variety of different nucleic acid molecules (i.e. a population having a variety of different sequences) are sequenced. The molecules can optionally be attached to a surface in a vessel. The nucleic acids can be attached at unique sites on the surface and single nucleic acid molecules that are spatially distinguishable one from the other can be sequenced in parallel. Alternatively, the nucleic acids can be amplified on the surface to produce a plurality of surface attached ensembles. The ensembles can be sequenced in parallel and detected in a spatially distinguishable way using methods and apparatus of the present disclosure.

A method set forth herein can use any of a variety of amplification techniques in a vessel. Exemplary techniques that can be used include, but are not limited to, polymerase chain reaction (PCR), rolling circle amplification (RCA), multiple displacement amplification (MDA), bridge amplification, or random prime amplification (RPA). In particular embodiments, one or more primers used for amplification can be attached to a surface in a vessel. In such embodiments, extension of the surface-attached primers along template nucleic acids will result in copies of the templates being attached to the surface. Methods that result in one or more sites on a solid support, where each site is attached to multiple copies of a particular nucleic acid template, can be referred to as "clustering" methods.

In PCR embodiments, one or both primers used for amplification can be attached to a surface. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. Nos. 5,641,658 or 7,115,400; U.S. Patent Pub. Nos. 2002/0055100 A1, 2004/0096853 A1, 2004/0002090 A1, 2007/0128624 A1 or 2008/0009420 A1, each of which is incorporated herein by reference. PCR amplification can also be carried out with one of the amplification primers attached to the surface and the second primer in solution. An exemplary format that uses a combination of one solid phase-attached primer and a solution phase primer is known as primer walking and can be carried out as described in U.S. Pat. No. 9,476,080, which is incorporated herein by reference. Another example is emulsion PCR which can be carried out as described, for example, in Dressman et al., *Proc. Natl. Acad. Sci. USA* 100:8817-8822 (2003), WO 05/010145, or U.S. Patent Pub. Nos. 2005/0130173 A1 or 2005/0064460 A1, each of which is incorporated herein by reference.

RCA techniques can be used in a method set forth herein. Exemplary reagents that can be used in an RCA reaction and principles by which RCA produces amplicons are described, for example, in Lizardi et al., *Nat. Genet.* 19:225-232 (1998) or US Pat. App. Pub. No. 2007/0099208 A1, each of which is incorporated herein by reference. Primers used for RCA can be in solution or attached to a surface in a flow cell.

MDA techniques can also be used in a method of the present disclosure. Some reagents and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); or U.S. Pat. Nos. 5,455,166; 5,130,238; or 6,214,587, each of which is incorporated herein by reference. Primers used for MDA can be in solution or attached to a surface in a vessel.

In particular embodiments, a combination of the above-exemplified amplification techniques can be used. For example, RCA and MDA can be used in a combination wherein RCA is used to generate a concatemeric amplicon in solution (e.g. using solution-phase primers). The amplicon can then be used as a template for MDA using primers that are attached to a surface in a vessel. In this example, amplicons produced after the combined RCA and MDA steps will be attached in the vessel. The amplicons will generally contain concatemeric repeats of a target nucleotide sequence.

Nucleic acid templates that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Thus, a mixture of nucleic acids used herein can be derived from a biological source, synthetic source or amplification product. Primers used herein can be DNA, RNA or analogs thereof.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Nucleic acids can also be derived from a prokaryote such as a bacterium, *Escherichia coli, staphylococci* or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference. Cells, tissues, biological fluids, proteins and other samples can be obtained from these organisms and detected using an apparatus or method set forth herein.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. Nos. 6,355,431 or 9,045,796, each of which is incorporated herein by reference. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

The apparatus and methods of the present disclosure have been exemplified in the context of use for nucleic acid sequencing reactions. The apparatus and methods can be used for other analytical applications as well. Generally, analytical applications that are carried out in scanning microscopes can be applied to apparatus and methods of the present disclosure. For example, the methods or apparatus can be configured to scan microarrays that are used for analyzing enzyme activity, binding of ligands to receptors, binding of complementary nucleic acids to each other, presence of mutations (such as single nucleotide polymorphisms (SNPs)) in nucleic acids, expression level for RNA species. Microarrays that are detected via optical labels, such as fluorophores, are particularly applicable. Larger biological samples such as cells or tissues can be detected using a method or apparatus herein. Other uses include evaluation of manufactured products for which quality or other characteristics are evaluated via microscopic scanning.

Exemplary products include, but are not limited to, computer chips, sensors, electronic components and other devices that are microfabricated or nanofabricated. Tests known in the art of molecular diagnostics can be modified for use in an apparatus or method set forth herein such as binding assays (e.g. enzyme-linked immunosorbent assay (ELISA)), real time polymerase chain reaction assays and the like. Real time polymerase chain reaction and quantitative polymerase chain reaction methods that employ optical detection techniques can employ focus sensing apparatus and methods set forth herein.

Terms used herein will be understood to take on their ordinary meaning in the relevant art unless specified otherwise. Several terms used herein and their meanings are set forth below.

The term "comprising" is intended herein to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

What is claimed is:

1. An apparatus for evaluating focus, comprising
   (a) a stage configured to hold a specimen; and
   (b) an optical train comprising a radiation source, a collimator, a primary beam splitter, a calibration beam splitter, an objective, and a detector,
   the optical train forming a first path wherein radiation from the radiation source is collimated by the collimator, then transmitted to the primary beam splitter, then to the calibration beam splitter, then a first portion of the radiation continues on the first path from the calibration beam splitter to the primary beam splitter, then to the detector, thereby forming a first image on the detector,
   wherein a second portion of the radiation follows a second path from the calibration beam splitter then through the objective to the specimen,
   wherein the optical train forms a third path wherein radiation from the specimen is transmitted through the objective, then through the calibration beam splitter, then through the primary beam splitter, then to the detector, thereby forming a second image on the same detector, and
   wherein the optical train comprises an astigmatism generator between the radiation source and the calibration beam splitter.

2. The apparatus of claim 1, further comprising an error detection circuit configured to receive data for the first image and programmed to determine a calibration state for the optical train from the data for the first image.

3. The apparatus of claim 2, further comprising the error detection circuit configured to receive data for the second image and programmed to determine a focus state for the apparatus from the data for the second image and from the calibration state.

4. The apparatus of claim 3, wherein the focus state and the calibration state are determined using the same error detection circuit.

5. The apparatus of claim 4, further comprising a z-actuator configured to adjust a relative position of the objective and the stage in response to instructions from the error detection circuit.

6. The apparatus of claim 1, wherein the astigmatism generator comprises an astigmatic optical surface.

7. The apparatus of claim 6, wherein the astigmatic optical surface comprises a toric surface of the primary beam splitter, the toric surface configured to reflect collimated radiation to the calibration beam splitter.

8. The apparatus of claim 7, wherein the toric surface has a toroid radius between 2000 mm and 5000 mm.

9. The apparatus of claim 6, wherein the astigmatic optical surface comprises a cylindrical lens.

10. The apparatus of claim 6, wherein the astigmatic optical surface comprises a crossed cylindrical lens pair.

11. The apparatus of claim 1, wherein the objective has a numerical aperture of 0.1 to 0.9.

12. The apparatus of claim 11, wherein the objective has a field of view between 0.1 mm$^2$ and 4 mm$^2$.

13. A nucleic acid sequencing system, comprising
the apparatus of claim 1; and
a luminescence optical train for directing radiation from an excitation radiation source through the objective to the specimen and for directing luminescent emission radiation from the specimen through the objective to a luminescence detector.

14. The nucleic acid sequencing system of claim 13, wherein the radiation source is a separate component from the excitation radiation source.

15. The nucleic acid sequencing system of claim 13, wherein the detector is a separate component from the luminescence detector.

16. The nucleic acid sequencing system of claim 13, wherein the specimen comprises an array of nucleic acids in a flow cell.

17. The nucleic acid sequencing system of claim 16, further comprising a fluidic system configured to deliver nucleic acid sequencing reagents to the flow cell.

18. The nucleic acid sequencing system of claim 16, wherein the optical train is configured to form the first image and the second image from radiation that is reflected from a surface of the flow cell.

19. The apparatus of claim 1, wherein the optical train further comprises an imaging lens placed between the primary beam splitter and the detector in the first path and in the third path.

20. A focusing method, comprising
(a) transmitting collimated radiation through a focusing apparatus to a primary beam splitter, then to a calibration beam splitter, wherein a first portion of the collimated radiation from the calibration beam splitter is transmitted by the primary beam splitter, to form a first image on a detector, wherein an astigmatism is generated in the collimated radiation prior to being transmitted to the calibration beam splitter;
(b) transmitting a second portion of the collimated radiation from the calibration beam splitter through an objective to a vessel, wherein collimated radiation is reflected from the vessel;
(c) transmitting the reflected radiation through the objective, then through the calibration beam splitter, then through the primary beam splitter to form a second image on the same detector;
(d) determining a calibration state for the focusing apparatus from the first image;
(e) determining a focus correction from the second image and from the calibration state; and
(f) adjusting a relative position of the objective and the vessel according to the focus correction.

21. An apparatus for evaluating focus, comprising
(a) a stage configured to hold a specimen; and
(b) an optical train comprising a radiation source, a calibration optic, an objective, and detector,
the optical train forming a first path wherein radiation from the radiation source is directed to the calibration optic and then a first portion of the radiation is directed to the detector, thereby forming a first image on the detector,
wherein a second portion of the radiation follows a second path from the calibration optic then through the objective to the specimen,
wherein the optical train forms a third path wherein radiation reflected from the specimen is transmitted through the objective, then to the detector, thereby forming a second image on the same detector, and
wherein the radiation that forms the first image is astigmatic.

22. A focusing method, comprising
(a) transmitting radiation through a focusing apparatus to a calibration optic that directs a first portion of the radiation to a detector, thereby forming a first image on the detector, wherein the radiation that forms the first image is astigmatic
(b) transmitting a second portion of the radiation from the calibration optic through an objective to a vessel, wherein radiation is reflected from the vessel;
(c) transmitting the reflected radiation through the objective, then to the detector, thereby forming a second image on the same detector;
(d) determining a calibration state for the focusing apparatus from the first image;
(e) determining a focus correction from the second image and from the calibration state; and
(f) adjusting a relative position of the objective and the vessel according to the focus correction.

* * * * *